US011041147B2

(12) United States Patent
Ricard et al.

(10) Patent No.: US 11,041,147 B2
(45) Date of Patent: Jun. 22, 2021

(54) **BACTERIOPHAGE STRAIN CAPABLE OF PRODUCING A LYTIC INFECTION IN THE *ESCHERICHIA COLI* ST131-025B:H4 CLONE**

(71) Applicants: INSERM (INSTITUT NATIONAL DE LA SANTÉ ET DE LA RECHERCHE MÉDICALE), Paris (FR); ASSISTANCE PUBLIQUE-HÔPITAUX DE PARIS (APHP), Paris (FR); UNIVERSITÉ PARIS DIDEROT—PARIS 7, Paris (FR); INSTITUT PASTEUR, Paris (FR); UNIVERSITÉ PARIS XIII PARIS-NORD, Villetaneuse (FR)

(72) Inventors: Jean-Damien Ricard, Paris (FR); Olivier Clermont, Paris (FR); Laurent Debarbieux, Paris (FR); Erick Denamur, Paris (FR); Nicolas Dufour, Cergy-Pontoise (FR)

(73) Assignees: INSERM (INSTITUT NATIONAL DE LA SANTÉ ET DE LA RECHERCHE MÉDICALE, Paris (FR); ASSISTANCE PUBLIQUE—HOPITAUX DE PARIS (APHP), Paris (FR); UNIVERSITÉ PARIS DIDEROT—PARIS 7, Paris (FR); UNIVERSITÉ PARIS XIII PARIS-NORD, Villentaneuse (FR)

( * ) Notice: Subject to any disclaimer, the term of this patent is extended or adjusted under 35 U.S.C. 154(b) by 118 days.

(21) Appl. No.: 16/093,361

(22) PCT Filed: Apr. 12, 2017

(86) PCT No.: PCT/EP2017/058871
§ 371 (c)(1),
(2) Date: Oct. 12, 2018

(87) PCT Pub. No.: WO2017/178561
PCT Pub. Date: Oct. 19, 2017

(65) Prior Publication Data
US 2019/0119652 A1 Apr. 25, 2019

(30) Foreign Application Priority Data
Apr. 13, 2016 (EP) .................................... 16305432

(51) Int. Cl.
| | | |
|---|---|---|
| *C12N 7/00* | (2006.01) | |
| *A61K 35/76* | (2015.01) | |
| *C07K 14/005* | (2006.01) | |
| *A61P 31/00* | (2006.01) | |

(52) U.S. Cl.
CPC ............. *C12N 7/00* (2013.01); *A61K 35/76* (2013.01); *A61P 31/00* (2018.01); *C07K 14/005* (2013.01); *C12N 2795/10221* (2013.01); *C12N 2795/10232* (2013.01)

(58) Field of Classification Search
None
See application file for complete search history.

(56) References Cited

FOREIGN PATENT DOCUMENTS

WO 2015/104388 A1 7/2015

OTHER PUBLICATIONS

Barrow, Paul; et al; "Use of Lytic Bacteriophage for Control of Experimental *Escherichia coli* Septicemia and Meningitis in Chickens and Calves" Clinical and Diagnostic Laboratory Immunology, 5, 294-298, 1998 (Year: 1998).*
F. Pouillot et el: "Efficacy of Bacteriophage Therapy in Experimental Sepsis and Meningitis Caused by a Clone 025b: H4-ST131 *Escherichia coli* Strain Producing CTX-M-15", Antimicrobial Agents and Chemotherapy, vol. 56, No. 7, Jul. 1, 2012, pp. 3568-3575.
M.-H Nicolas-Chanoine et al: "*Escherichia coli* ST131, an Intriguing Clonal Group", Clinical Microbiology Reviews, vol. 27, No. 3, Jun. 30, 2014, pp. 543-574.
B. A. Rogers et al: "*Escherichia coli* 025b-ST131: a pandemic, multiresistant, community-associated strain", Journal of Antimicrobial Chemotherapy, vol. 66, No. 1, Jan. 1, 2011, pp. 1-14.
Reardon Sara: "Phage therapy gets revitalized", Nature, Nature Publishing Group, United Kingdom, vol. 510, No. 7503, Jun. 5, 2014, pp. 15-16.
Szijártó Valéria et al: "Bactericidal monoclonal antibodies specific to the lipopolysaccharide 0 antigen from multidrug-resistant *Escherichia coli* clone ST131-025b:H4 elicit protection in mice", Antimicrobial Agents and Chemotherapy, American Society for Microbiology, US, vol. 59, No. 6, Jun. 1, 2015, pp. 3109-3116.
Nicolas Dufour, et al., "The Lysis of Pathogenic *Escherichia coil* by Bacteriophages Releases Less Endotoxin Than by β-Lactams," CID 2017:64 (Jun. 1) 1582-1588.

(Continued)

*Primary Examiner* — David W Berke-Schlessel
(74) *Attorney, Agent, or Firm* — Arrigo, Lee, Guttman & Mouta-Bellum LLP

(57) ABSTRACT

The present invention relates to a bacteriophage strain capable of producing a lytic infection in the *Escherichia coli* ST131-025b:H4 clone. The burden of ST131-025b:H4 *Escherichia coli* clonal complex in human community and hospital-acquired infections is increasing worldwide, going along with a worrying and growing resistance to betalactams and fluoroquinolones. Bacteriophage LM33_P1 infects exclusively (100% specificity) 025b *E. coli* strains with 70% coverage on the two major antibiotic resistant pandemic clonal complexes ST131-025b:H4 and ST69-025b. The inventors evaluated the in vivo activity of bacteriophage LM33_P1 using three different extraintestinal virulence murine models and showed that it infects bacteria in several organs. In particular, the invention relates to a bacteriophage capable of producing a lytic infection in the *Escherichia coli* ST131-025b:H4 clone comprising a polypeptide corresponding to the bacteriophage tail fiber protein and responsible for the attachment of the bacteriophage to the *Escherichia coli* ST131-025b:H4 clone.

Figure 1:
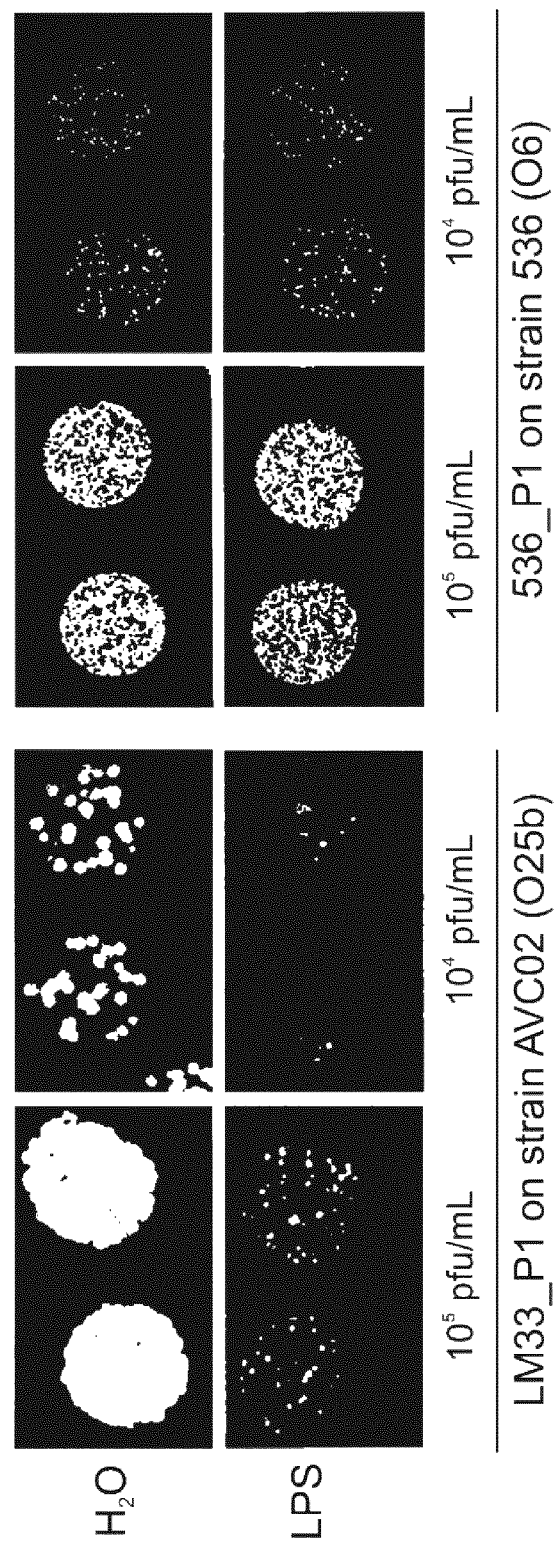

20 Claims, 5 Drawing Sheets
Specification includes a Sequence Listing.

(56) References Cited

OTHER PUBLICATIONS

Icolas Dufour, et al., "Phage Therapy of Pneumonia Is Not Associated with an Overstimulation of the Inflammatory Response Compared to Antibiotic Treatment in Mice," Antimicrobial Agents and Chemotherapy, Aug. 2019 vol. 63 Issue 8 e00379-19.
Nicolas Dufour, et al., "Bacteriophage LM33_P1, a fast-acting weapon against the pandemic ST131-O25b:H4 *Escherichia coli* clonal complex," J Antimicrob Chemother doi:10.1093/jac/dkw253, Jul. 7, 2016.
Dean Scholl, et al., "An Engineered R-Type Pyocin Is a Highly Specific and Sensitive Bactericidal Agent for the Food-Borne Pathogen *Escherichia coli* O157:H7," Antimicrobial Agents and Chemotherapy, Jul. 2009, vol. 53, No. 7, p. 3074-3080.

\* cited by examiner

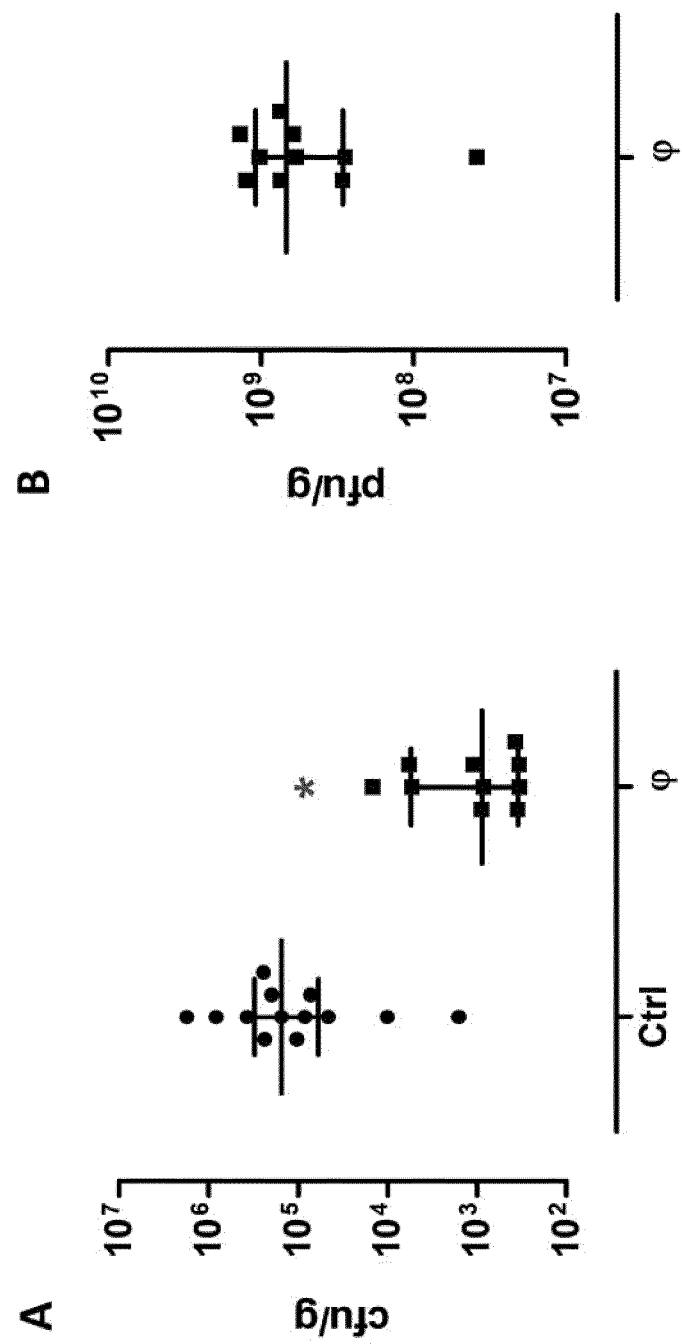

BACTERIOPHAGE STRAIN CAPABLE OF PRODUCING A LYTIC INFECTION IN THE *ESCHERICHIA COLI* ST131-O25B:H4 CLONE

FIELD OF THE INVENTION

The present invention relates to a bacteriophage strain capable of producing a lytic infection in the *Escherichia coli* ST131-O25b:H4 clone.

BACKGROUND OF THE INVENTION

Amongst the highly diverse *Escherichia coli* population (1), the ST131-O25b:H4 clonal complex is of particular concern. Since its first description in 2008 in a limited number of countries, this clone is now present worldwide demonstrating an uncommon ability to propagate in humans (2, 3). Moreover, ST131-O25b:H4 *E. coli* strains have a high pathogenic potential (4), they belong to the B2 phylogroup where most extraintestinal-pathogenic *E. coli* classify (5), they express a large number of virulence factors (6) and are lethal in a mouse model of sepsis (7). Involved in community as well as hospital-acquired infections, ST131-O25b:H4 isolates are responsible for a wide range of pathology, from the common cystitis to the life threatening meningitis (2). Finally, these clones are also particularly worrisome as they are associated with a high level of resistance to betalactams (mainly via production of CTX-M-15 extended spectrum beta-lactamase but also carbapenemase (8)) and fluoroquinolones (9, 10). To a lesser extent, O25b strains may belong to another antibioresistant spreading clonal complex with a high extraintestinal pathogenic potential, the ST69 (clonal group A) (11). The lack of new antibiotics and the worldwide continuous increase of infections caused by multidrug resistant bacterial pathogens have revived attention to phage therapy (12), boosting the search for novel bacteriophages. Numerous experimental data have been published demonstrating the proof of concept of this approach and clinical trials have been reported or are ongoing.

SUMMARY OF THE INVENTION

The present invention relates to a bacteriophage strain capable of producing a lytic infection in the *Escherichia coli* ST131-O25b:H4 clone. In particular, the present invention is defined by the claims.

DETAILED DESCRIPTION OF THE INVENTION

The burden of ST131-O25b:H4 *Escherichia coli* clonal complex in human community and hospital-acquired infections is increasing worldwide, going along with a worrying and growing resistance to betalactams and fluoroquinolones. Bacteriophage LM33_P1, isolated using an extended spectrum beta-lactamase-producing ST131-O25b:H4 strain responsible for a ventilator-associated pneumonia, infects exclusively (100% specificity) O25b *E. coli* strains with 70% coverage on the two major antibiotic resistant pandemic clonal complexes ST131-O25b:H4 and ST69-O25b. The inventors showed that bacteriophage specificity relied on a LPS-dependent interaction. Remarkably, bacteriophage LM33_P1 displays uncommon adsorption and kinetic characteristics leading to bacteria lysis in less than 10 minutes. The inventors evaluated the in vivo activity of bacteriophage LM33_P1 using three different extraintestinal virulence murine models, i.e. pneumonia, sepsis and urinary tract infection and showed that it infects bacteria in several organs. This bacteriophage represents a promising specific tool targeting O25b *E. coli* strains from which therapeutic approaches could be developed to stop, or at least slow down, the spread of this drug resistant clonal complex.

Accordingly a first object of the present invention relates to a bacteriophage capable of producing a lytic infection in the *Escherichia coli* ST131-O25b:H4 clone comprising a polypeptide having an amino acid sequence having at least 80% of identity with the amino acid sequence of SEQ ID NO:1 wherein said polypeptide corresponds to the bacteriophage tail fiber protein and is responsible for the attachment of the bacteriophage to the *Escherichia coli* ST131-O25b:H4 clone.

SEQ ID NO: 1

MSTITQFPSGNTQYRIEFDYLARTFVVVTLVNSSNPTLNRVLEVGRDYRF

LNPTMIEMLADQSGFDIVRIHRQTGTDLVVDFRNGSVLTASDLTNSELQA

IHIAEEGRDQTVDLAKEYADAAGSSAGNAKDSEDESRRIAASIKAAGKIG

YITRRSFEKGFNVTTWNEVLLWEEDGDYYRWDGTLPKNVPAGSTPESSGG

IGLSAWVSVGDASLRANLADSDGAKYIGSGERTLLEHNNDVLHSKDFPTL

QAAIDASLQKNDLLVSPGNYTEKVTIGNAQLKGVGGATVLKTPADFTNTV

QVNLATPHWQFRHSGGFAIDGSGTTGAVGISFDPSDQYSGRHNFSDVYIH

NINKAIQKPSGNIGNTWRNIGISTCDWGYYAISGSEMHCGADTLYNIHFD

GISTYAVYLDGTVDNGGGGAWWLKDSIIEASGGGGIYLKSKSGDCPTSPC

GVSNIWMEAIATSPAVQVDGVAQKPRVLKLVDTAIFFAEYSYLNNIELSN

SNLVTYGCRFDNADGNQDIVVDAQSTIVAHDVYLNGSSGKDVIVESVASQ

SATIAATNLSLRGNLTRGRVFNTPTGNKLMAITFDSGSHNFSGSGTVNGS

TVSDGLHAATCTEFSFPGAGLYEMVATRTTITSGRWYVWGVNSRLQSGSA

DISITSGITMGSVYTKPGEWISTFGVGKASTTGTVALYVSTGGGSGATVR

FSDFFIAEFTTQAQALAFANSRMSLS

According to the invention a first amino acid sequence having at least 80% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

In some embodiments, bacteriophage of the present invention comprises a genomic sequence having at least 70% of identity with the genomic sequence of LM33_P1 represented by SEQ ID NO:2.

According to the invention a first nucleic acid sequence having at least 70% of identity with a second nucleic acid sequence means that the first nucleic acid sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second nucleic acid sequence.

In some embodiments, the bacteriophage of the present invention is the bacteriophage strain LM33-P1 deposited at the French National Collection of Microorganisms at the Institut Pasteur under Accession Number CNCM 1-4964 on Apr. 3, 2015 or a variant thereof, wherein the variant has the same lytic activity, preferably the same lytic activity and the same phenotypic characteristics as said bacteriophage strain.

In some embodiments, the variant of LM33-P1 is a progeny of the bacteriophage strain LM33-P1. The term "progeny" means bacteriophage replicates containing descendents produced according to subculture of the deposited bacteriophage or a method known to those ordinarily skilled in the art, or bacteriophages having a RFLP (Restriction fragment length polymorphism) DNA profile substantially equivalent to the deposited bacteriophage. The term "have a substantially equivalent or equal RFLP" is expressed to represent variability between organisms according to the method suggested by Tenover et al. (Tenover, F. C. et al. Interpreting Chromosomal DNA Restriction Patterns Produced by Pulsed-Field Gel Electrophoresis: Criteria for Bacterial Strain Typing. J. Clin. Microbiol 33:2233-2239 (1995)). It is also possible to select appropriate phages based upon the sequences of DNA or RNA encoding proteins involved in the binding and/or entry of phage into their specific host, or based upon the amino acid sequences or antigenic properties of such proteins.

Typically, the variants are tested for activity against multiple strains to select broad-spectrum O25b-ST131-active bacteriophage. Efforts are made to select phages that (i) are lytic, and (ii) are specific to ST131-O25b:H4 clones. Typically methods for evaluating the lytic properties of the variants are described in the EXAMPLE.

Suitable methods for isolating pure bacteriophage strains from a bacteriophage-containing sample are well known, and such methods may be adapted by the skilled artisan in view of the guidance provided herein. Isolation of active bacteriophage from suitable samples typically proceeds by mixing the sample with nutrient broth, inoculating the broth with a host bacterial strain, and incubating to enrich the mixture with bacteriophage that can infect the host strain. A *Escherichia coli* ST131-O25b:H4 clone will be used as the host strain. After the incubation for enrichment, the mixture is filtered to remove bacteria, leaving lytic bacteriophage in the filtrate. Serial dilutions of the filtrate are plated on a lawn of bacteria, and active phages infect and lyse neighbouring bacteria. However the agar limits the physical spread of the phage throughout the plate, resulting in small visibly clear areas called plaques on the plate where bacteriophage has destroyed the bacteria within the confluent lawn of growth. Since one plaque with a distinct morphology represents one phage particle that replicated in the bacteria within that area of the bacterial lawn, the purity of a bacteriophage preparation can be ensured by removing the material in that plaque with a pasteur pipette (a "plaque pick") and using this material as the inoculum for further growth cycles of the phage. The bacteriophage produced in such cycles represents a single strain or "monophage." The purity of phage preparation (including confirmation that it is a monophage and not a polyvalent phage preparation) is assessed by a combination of electron microscopy, SDS-PAGE, DNA restriction digest, analytical ultracentrifugation and cross-test against various bacterial strains. In addition, each phage is uniquely identified by its DNA restriction digest profile, protein composition, and/or genome sequence.

Quantities of broad-spectrum bacteriophage needed for therapeutic uses described below may be produced by culture on a suitable host strain in the manner described above for enrichment culture. When performing an enrichment culture to produce bacteriophage for therapeutic use, a host strain is selected based on its ability to give a maximum yield of phage, as determined in pilot experiments with several different host *Escherichia coli* ST131-O25b:H4 clones.

The bacteriophage of the present invention is particularly suitable for therapeutically purposes.

Accordingly a further aspect of the present invention relates to a method of treating an infection caused by an *Escherichia coli* ST131-O25b:H4 clone in a patient in need thereof, comprising administering to the patient a therapeutically effective amount of the bacteriophage of the present invention.

As used herein, the term "treatment" or "treat" refers to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

For example any patient who is at risk for colonization with the *Escherichia coli* ST131-O25b:H4 clone or who has proven the *Escherichia coli* ST131-O25b:H4 clone colonization is a candidate for treatment according to the method of the present invention.

Typically, the method of the present invention is particularly suitable for the treatment of nosocomial infections and in particular, hospital-acquired nosocomial infections.

In some embodiments, the bacteriophage of the present invention is particularly suitable for the treatment of an infectious disease selected from the group consisting of cystic fibrosis, otitis media, keratitis, endophthalmitis, bacteremia, burn wound infection, pneumonia, meningitis, peritonitis, urinary tract infections or sepsis, more preferably pneumonia, urinary tract infections, meningitis, peritonitis or sepsis, and most preferably urinary tract infection, peritonitis or sepsis.

In some embodiments, the bacteriophage of the present invention is particularly suitable for the treatment of urinary tract infection.

In some embodiments, the bacteriophage of the present invention is particularly suitable for the treatment of lung infection.

In some embodiments, the patient is selected among immunocompromised and/or seriously ill patients in cancer centers, intensive care units, and organ transplant centers.

The *Escherichia coli* ST131-O25b:H4 clone infection is a particularly serious problem among immunocompromised and/or seriously ill patients in cancer centers, intensive care units, and organ transplant centers. For example, categories of immunocompromised patients who would be susceptible to the *Escherichia coli* ST131-O25b:H4 clone colonization include: 1) leukemia (30,200 patients per year in the U.S.) and lymphoma patients (64,000 patients per year in the U.S.), 2) transplant patients (20,961 per year in the U.S.), and 3) AIDS patients (66,659 patients per year in the U.S.).

According to this invention, the bacteriophage of the present invention is formulated in pharmaceutical compositions containing the bacteriophage and a pharmaceutically acceptable carrier, and can be stored as a concentrated aqueous solution or lyophilized powder preparation. A pharmaceutically acceptable carrier or excipient refers to a non-toxic solid, semi-solid or liquid filler, diluent, encapsulating material or formulation auxiliary of any type. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Sterile injectable solutions are prepared by incorporating the bacteriophage of the present invention in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Bacteriophage may also be formulated for oral administration by resuspending purified phage preparation in aqueous medium, such as deionized water, mineral water, 5% sucrose solution, glycerol, dextran, polyethylene glycol, sorbitol, or such other formulations that maintain phage viability, and are non-toxic to humans. The pharmaceutical composition may contain other components so long as the other components do not reduce the effectiveness (infectivity) of the bacteriophage so much that the therapy is negated. Pharmaceutically acceptable carriers are well known, and one skilled in the pharmaceutical art can easily select carriers suitable for particular routes of administration (Remington's Pharmaceutical Sciences, Mack Publishing Co., Easton, Pa., 1985).

The pharmaceutical compositions may be administered by parenteral (subcutaneously, intramuscularly, intravenously, intraperitoneally, intrapleurally, intravesicularly or intrathecally), topical, oral, rectal, inhalation, ocular, auricular, or nasal route, as necessitated by choice of drug and disease. Injection of specific lytic phages directly into the bloodstream can eliminate or significantly reduce the number of targeted bacteria in the blood. If, after either oral or local administration, phages get into the bloodstream in sufficient numbers to eliminate bacteria from the bloodstream, septicemia may be treated by administering phages orally (or locally). If the phages do not get into the bloodstream in sufficient numbers to eliminate bacteria from the bloodstream, the utility of direct i.v. injection of phages for treating septic infections can be used to treat bloodstream infections and other pathogenic bacteria, and can provide an urgently needed means for dealing with currently untreatable septicemic infections. The phage may be administered orally in, for example, mineral water, optionally with 2.0 grams of sodium bicarbonate added to reduce stomach acidity. Alternatively, sodium bicarbonate may be administered separately to the patient just prior to dosing with the phage. Phages also may be incorporated in a tablet or capsule which will enable transfer of phages through the stomach with no reduction of phage viability due to gastric acidity, and release of fully active phages in the small intestine. For non-oral administration, the composition of the present invention may be formulated into injections for subcutaneous, intravenous, or intramuscular routes, suppositories, or sprays inhalable via the respiratory tract, such as aerosols. Injection preparations may be obtained by dissolving or suspending the composition of the present invention, together with a stabilizer or a buffer, in water and packaging the solution or suspension in ampules or vial units. For sprays, such as aerosol, a propellant for spraying a water-dispersed concentrate or wetting powder may be used in combination with an additive.

As used herein, the term "effective amount" refers to a quantity sufficient to achieve a therapeutic effect (e.g. treating the infection). In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The dose of the bacteriophage and duration of therapy for a particular patient can be determined by the skilled clinician using standard pharmacological approaches in view of the above factors. The response to treatment may be monitored by, analysis of blood or body fluid levels of ST131-O25b:H4 clone, or ST131-O25b:H4 clone levels in relevant tissues or monitoring disease state in the patient. The skilled clinician will adjust the dose and duration of therapy based on the response to treatment revealed by these measurements. Based on previous human experience, a dose of phage between $10^7$ and $10^{11}$ PFU will be suitable in most instances.

The bacteriophage of the present invention is also particularly suitable for environmental applications. For example, environmental applications of phage in health care institutions could lie most useful for equipment such as endoscopes and environments such as ICUs which may be potential sources of nosocomial infection by the *Escherichia coli* ST131-O25b:H4 clone but which may be difficult or impossible to disinfect. Phage would be particularly useful in treating equipment or environments inhabited by *Escherichia coli* ST131-O25b:H4 clones which may become resistant to commonly used disinfectants. Phage compositions used to disinfect inanimate objects or the environment may be sprayed, painted, or poured, onto such objects or surfaces in aqueous solutions with phage titers ranging between $10^7$-$10^{11}$ PFU/ml. Alternatively, phage may be applied by aerosolizing agents that might include dry dispersants which would facilitate distribution of the phage into the environment. Such agents may also be included in the spray if compatible with phage viability and nontoxic in nature. Finally, objects may be immersed in a solution containing phage. The optimal numbers and timing of applications of phage compositions remains to be determined and would be predicated by the exact usage of such products. The bacteriophage of the present invention can also be suitable for decontaminate food products.

The invention will be further illustrated by the following figures and examples. However, these examples and figures should not be interpreted in any way as limiting the scope of the present invention.

FIGURES

FIG. 1. O25b LPS extract inhibits bacteriophage LM33_P1 infection: appearance on agar plates. LPS extract from strain LM33 was mixed with bacteriophage LM33_P1 (left) or 536_P (right) at two different concentrations ($10^5$ and $10^4$ pfu/mL) and assayed on two agar plates overlaid with an O25b strain (AVC02) or an O6 strain (536) as control. Enlargements of these two plates are shown to facilitate the observation.

Figure 2:
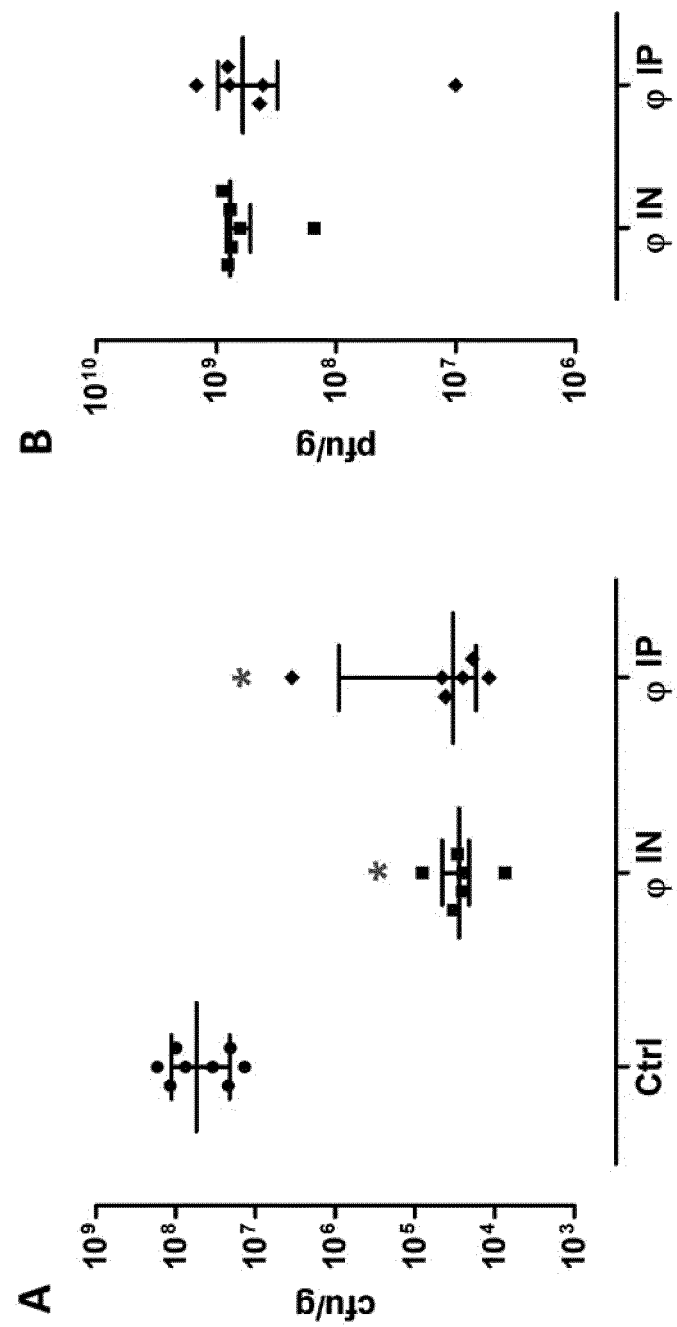

FIG. 2. Bacteriophage LM33_P1 in vivo activity in a lung infection model. Bacterial (A) and viral (B) counts 17 hours post-infection in lungs homogenate of mice infected with $1×10^8$ cfu of strain LM33. Four hours post-infection, mice received either PBS (Ctrl, n=8, intranasally and intraperitoneally) or bacteriophage LM33_P1 by intranasal route (φ IN, MOI 50, n=6) or by intraperitoneal route (φ IP, MOI 500, n=6). Results are expressed as individual values with median and interquartile ranges ($25^{th}$ and $75^{th}$ percentiles). *: $p<0.001$ compared to control group.

Figure 3A:
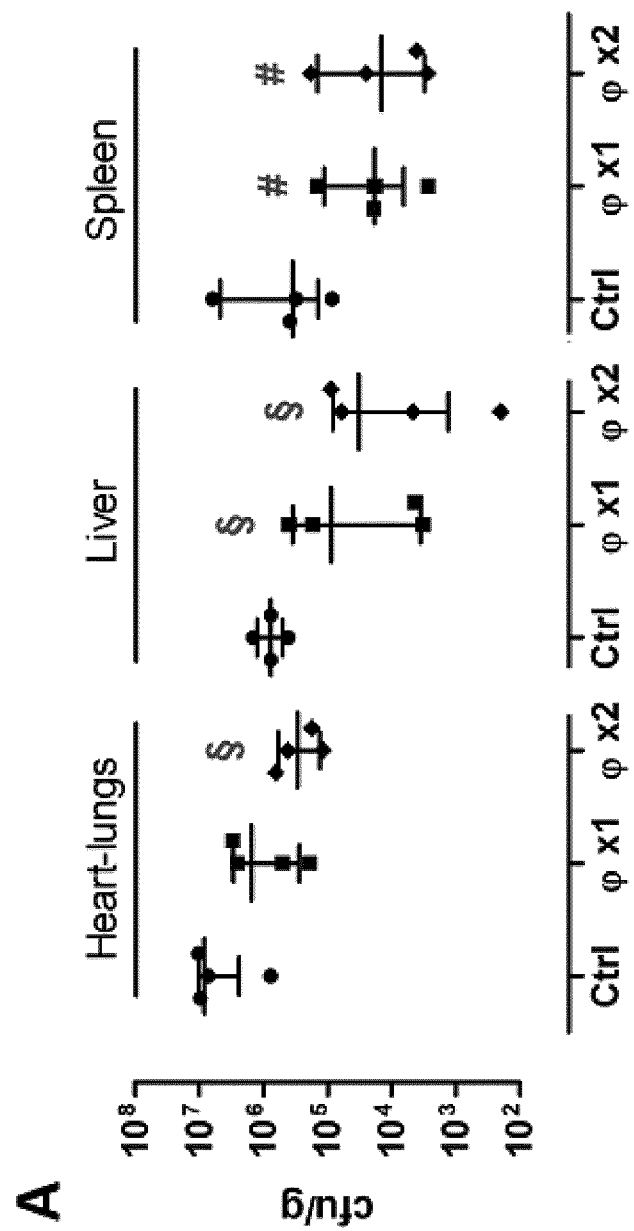
Figure 3B:
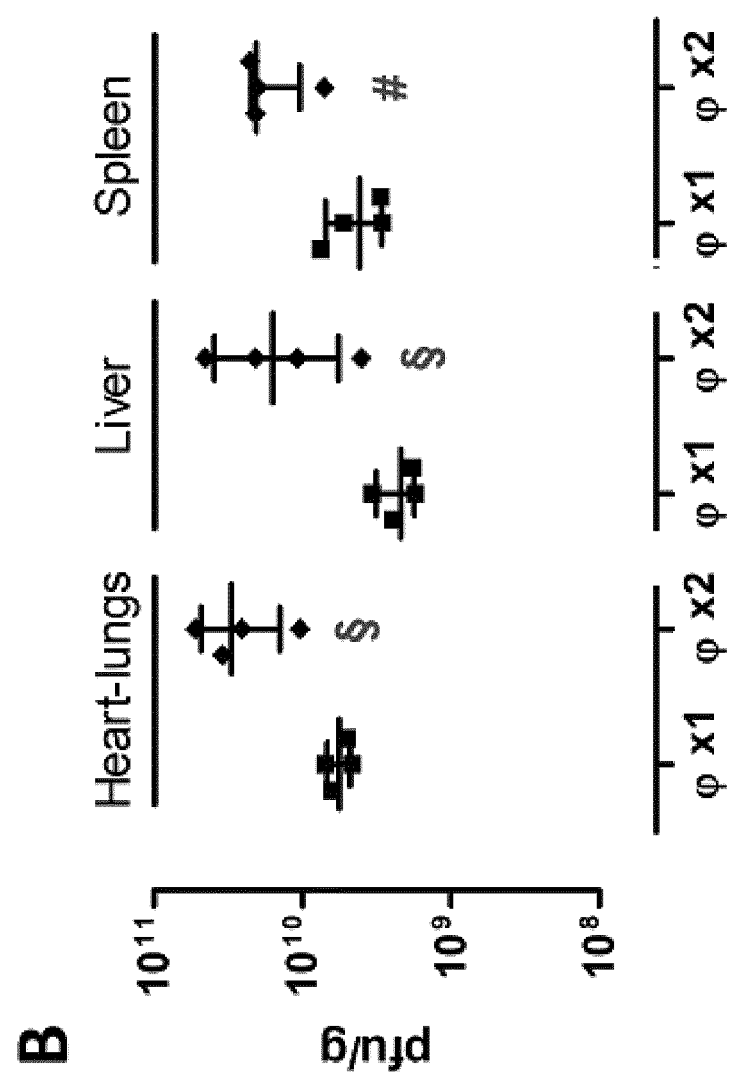

FIG. 3. Bacteriophage LM33_P1 in vivo activity in a septicemia model. Bacterial (A) and viral (B) counts 20 hours post-infection in indicated organs of mice infected with $1×10^9$ cfu of strain H1659 (ST131-O25b:H4). Two hours post-infection, mice received intraperitoneally either PBS (Ctrl) or bacteriophage LM33_P1 at a MOI of 60 (φ X1: one dose 2 hours post-infection, φ X2: two doses 2 and 12 hours post-infection). Results are expressed as individual values (4 animals per condition) with median and interquartile ranges ($25^{th}$ and $75^{th}$ percentiles). §: $p<0.05$ compared to control group, #: $p=0.057$ compared to control group.

FIG. 4. Bacteriophage LM33_P1 in vivo activity in a urinary tract infection model. Bacterial (A) and viral (B) counts 48 hours post-infection in kidneys homogenates of mice infected with $5×10^7$ cfu of strain LM33. Twenty four hours post-infection, mice received intraperitoneally either PBS (Ctrl, n=13) or bacteriophage LM33_P1 (φ, MOI 200, n=10). Results are expressed as individual values with median and interquartile ranges ($25^{th}$ and $75^{th}$ percentiles). *: $p<0.001$ compared to control group.

EXAMPLE

Material & Methods

Bacterial Strains and Bacteriophages, Susceptibility Testing

Bacterial strains used in this work belong to previously published collections of human commensal and extraintestinal *E. coli* gathered in France during the 2010s (13-15), from the ECOR collection (16) and the ColoColi collection (an ongoing French multicenter study collecting *E. coli* strains in the lower respiratory tract of mechanically ventilated patients). Phylogroup and ST belonging was determined as described in (17, 18). O-type and fimH allele were determined by PCR-based assays as previously described (19, 20), respectively. All strains were grown in lysogeny broth (LB) (Difco™ Bacto-Tryptone 10 g/L, Difco™ Yeast extract Difco 5 g/L, NaCl 5 g/L). Antibiotic susceptibility using the disk diffusion method was performed following the guidelines of the European Committee for Antimicrobial Susceptibility Testing guidelines.

Some *E. coli* strains, used for lipopolysaccharide (LPS) assays or bacteriophage susceptibility testing, are detailed below:

LM33, LM36, AVC02 (ST131-O25b:H4) and AVC03 (O25b, non-ST131) are clinical strains responsible for ventilator-associated pneumonia, 536 (ST127-O6), LM02 (ST69-O17) and ECOR51 (ST73-O25a) have been used as source of their corresponding LPS, 81009 WT (ST131-O25b:H4) and its isogenic rough derivative (mutant strain obtained by deleting the gene encoding for the O-antigen ligase) (21) were used to prove the LPS-dependent interaction of LM33_P1.

Bacteriophages were isolated from sewage, using specific host. By convention, bacteriophages are named as follows: "host bacteria_Px" (for example LM33_P1 represents the first bacteriophage isolated using strain LM33). In all competition experiments, bacteriophage solutions were purified using ultracentrifugation on cesium chloride gradient as previously described (22).

For bacteriophage susceptibility testing, we used double spot test (23) as screening method to identify resistant strains. Briefly, spot test consisted in dropping off 10 µL of a growing liquid culture of the bacterial strain ($OD_{600nm}$ 0.5) on an agar plate. After drying, 1 µL of the bacteriophage solution (LM33_P1, $10^7$ pfu/mL) was added on one half of the bacterial drop. Plate was then incubated at 37° C. during 4 hours before reading. A susceptible strain was identified by the presence of a crescent-shaped lysis area on the bacterial drop or the visualization of individualized plaques. Efficiency of plaquing (EOP) was determined for all susceptible strains by titrating the solution of LM33_P1 on both its host (LM33) and the evaluated strain. EOP was calculated as the ratio of number of plaques formed by the bacteriophage on the non-host strain to the number of plaques formed on its host, using the same bacteriophage solution. Only strains for which individualized plaques were observed were considered as susceptible strains. For strain 81009 WT and its rough derivative mutant, tests were performed at 20° C. to turn-off type II capsule expression (24).

LPS Extraction

LPS extracts were purified from the same amount of bacteria ($10^{10}$ cfu) using a hot phenol-water-diethyl ether extraction (25) followed by extensive dialysis against sterile pyrolyzed water. High purity LPS was confirmed by performing agarose gel electrophoresis with ethidium bromide staining (nucleic acids detection) and SDS-PAGE 12% followed by Coomassie blue staining (proteins detection). Ten µL of each LPS extract were migrated on a SDS-PAGE 10% followed by silver staining to visualize the LPS O-antigen pattern (SilverSNAP Stain Kit II, Pierce).

Plaques Inhibition Assays with LPS Extracts

From purified stock solution of bacteriophages in TN buffer (Tris-HCl 10 mM, NaCl 150 mM, pH 7.5), 3 solutions of $10^6$, 10 and $10^4$ pfu/mL in TN buffer were prepared. Each of these working solutions was used to prepare final tubes with bacteriophages alone (100 µL of working solution+100 µL of pyrolyzed water) and tubes with bacteriophages+LPS (100 µL+100 µL of undiluted LPS extract). Additional tubes containing bacteriophages and decreasing amounts of LPS were also prepared (pyrolyzed water was used to reach an identical final volume). Then, 10 µL of each final bacteriophage tubes, with and without LPS, were spotted in triplicate on an agar plate, previously overlaid by the bacteria to test. Plates were incubated during 4 hours at 37° C. before plaques-forming units were numerated in each condition.

Characterization of Bacteriophage LM33_P1

Adsorption assay and one-step growth were performed using LB (Difco™ Bacto-Tryptone 10 g/L, Difco™ Yeast extract Difco 5 g/L, NaCl 5 g/L), under constant shaking (100 rpm) at 37° C., as described by Hyman and Abedon (26), in triplicate. A correlation curve was extrapolated from raw data using nonlinear regressions (GraphPad Prism 5.0, GraphPad software, California): a dose-response model was used for one step growth experiment (Y=Bottom+(Top−Bottom)/(1+10^((Log EC50−X)*HillSlope)) with Y=log (pfu/infected cell) and X=time) and an exponential model with one phase decay for adsorption experiment (Y=(Y0−Plateau)*exp(−K*X)+Plateau with Y=free phages (%), X=time). Growth parameters (eclipse and latent period, burst size) were then derived from these regressions. Adsorption constant was calculated as −p/N where p is the slope of the straight line obtained after a natural logarithm transform and N the concentration of bacteria when starting the adsorption assay.

Lysis Kinetic (with and without LPS Extracts) and Aggregation Assays with O25 Antibody Lysis kinetics were performed as detailed in the SI. Briefly, the growth of LM33 with and without LM33_P1 was followed overtime by recording optical density at 600 nm every 15 minutes.

Aggregation assays were performed using O25 E. coli anti-serum (Statens Serum Institut, Copenhagen, Denmark) and observed under light microscope as detailed in the SI.

Sequencing of the Strain LM33 and Bacteriophage LM33_P1

Sequencing of bacteriophage LM33_P1 and strain LM33 was performed using Illumina sequencing technology (Illumina Inc., San Diego, Calif.). LM33_P1 DNA was extracted from a purified bacteriophage solution, using DNase and RNase pretreatments followed by a phenol-chloroform extraction, modified from Pickard (27). LM33 genomic DNA was extracted using a MaxWell Tissue DNA Purification kit (Promega, Madison, Wis.). Genomes annotation was performed by MicroScope plateform for strain LM33 and with RAST server for bacteriophage LM33_P1 (28, 29) followed by manual curation.

Murine Experimental Infections Models

Animal were housed in animal facilities in accordance with French and European regulations on the care and protection of laboratory animals. Protocols were approved by the veterinary staff of the Institut Pasteur and INSERM animal facilities as well as the National Ethics Committee regulating animal experimentation. Food and drink were provided ad libitum.

Pneumonia was initiated by intranasal administration of $1 \times 10^8$ cfu of strain LM33 on anesthetized eight-week-old 25 g BALB/cJRj male mice (Janvier, Le Genest Saint Isle, France) as previously described (30). Mice were treated using bacteriophage LM33_P1 four hours post-infection, either by using the intranasal route (multiplicity of infection of 50, i.e. a ratio of viruses to bacteria equal to 50) or the intraperitoneal route (MOI of 500). Control mice received accordingly an intranasal or intraperitoneal identical volume of PBS (phosphate-buffered saline). Lungs were collected 17 hours post-infection on euthanized animals.

The septicemia model, as previously described, is essentially used to study intrinsic extraintestinal virulence of E. coli isolates (7). Four-week-old 17 g OF1 female mice (Janvier, Le Genest Saint Isle, France) were injected subcutaneously into the nape of the neck with $1 \times 10^9$ cfu of strain H1659 (ST131-O25b:H4) (6). Because of the high inoculum used, we tested both a single and a double dose of bacteriophages: the single dose (MOI 60) was administered by intraperitoneal injection 2 hours post-infection while the double dose consisted in an injection (MOI 60) administered 2 and 12 hours post-infection. Control mice received an identical volume of PBS. Organs targeted by septic metastasis (heart-lung, spleen and liver) were collected on animals that died between 24 to 30 hours post-infection.

The urinary tract infection model consists in a retrograde kidneys infection occurring after an intra-urethral injection of $5 \times 10^7$ cfu of strain LM33 in the bladder, as previously described (31). Twenty-four hours after infection, 8-week-old 17 g CBA/j female mice (Charles River, Chatillon-sur-Chalaronne, France) were treated intraperitoneally with LM33_P1 (MOI of 200) while control mice received an identical volume of PBS. Kidneys were collected 48 hours post-infection.

In all cases, organs were mechanically homogenized in cold PBS using a gentleMACS Octo Dissociator (Milteny Biotec, Bergisch Gladbach, Germany) before being serially diluted and spread on Drigalski agar plates containing appropriate antibiotic to numerate colony. Bacteriophages count was performed on supernatant after centrifugation of homogenates according to routine methods.

Statistical Analysis

All statistical analyses were performed by using Graph-Pad Prism version 5.00 (GraphPad Software, La Jolla, Calif.). The normal distribution of all variables was checked using the Kolmogorov-Smirnov test, and results are then expressed as mean±SD. In case of non-Gaussian distribution, results are expressed as median [25th, 75th percentile]. Statistical tests (Student t test or Mann-Whitney test) were chosen accordingly.

Results:

Bacteriophage LM33_P1 Targets Antibiotic Resistant O25b E. coli Strains.

The E. coli strain LM33 (isolated from an intensive care unit patient who developed a ventilator-associated pneumonia) was used to isolate bacteriophage LM33_P1. Strain LM33 displays an O25b:H4 serotype, a B2 phylogroup (subgroup I) and a ST131 sequence-type as well as a multi-drug resistance phenotype with an extended spectrum beta-lactamase, a resistance to nalidixic acid, aminoglycosides (kanamycin, tobramycin, gentamicin, netilmicin excepted for amikacin where an intermediate phenotype is found), sulphonamides and chloramphenicol. The beta-lactam resistance is supported by a plasmid (pLM33) bearing the blaTEM-1c (penicillinase) and blaSHV-12 (extended spectrum beta-lactamase) genes, as well as by the bacterial chromosome containing the blaDHA-7 gene encoding a cephalosporinase and also a copy of the blaSHV-12 and blaTEM-1c gene (Table 1).

We determined the host range of bacteriophage LM33_P1 on a panel of 283 E. coli strains belonging to various O-types (data not shown). One hundred and eighty-three (64%) of these strains were not O25b and none of them was infected by LM33_P1, including twelve O25a strains and six ST131-O16 strains. Among the remaining one hundred O25b strains (encompassing 83 ST131, 4 ST69, 10 ST95 and 3 others STs), 64 (64%) were infected by LM33_P1 with a median efficiency of plaquing of 0.46 [0.09-1.27]. Interestingly, LM33_P1 was found to be more efficient on STs associated with high antibiotic resistance (ST131 and ST69) where 70% of these strains were lysed while it was weakly efficient on ST associated with low antibiotic resistance (ST95 and others) where only 23% of these strains were susceptible (data not shown). Finally, we did not find a correlation between susceptibility to bacteriophage LM33_P1 and the fimH allele H30, which is strongly associated with fluoroquinolone resistance among ST131 strains (32).

Bacteriophage LM33_P1 is a Podoviridae Distantly Related to Bacteriophage T7.

Genome of bacteriophage LM33_P1 (38 979 bp; GC content of 50.8%; 49 ORFs predicted) lacks putative ORFs with homologies to integrase or recombinase.

A BLAST analysis of the genomic sequence revealed that the four closest related bacteriophages were enterobacteria bacteriophages: three coliphages called PE3-1, K1F (33), EcoDS1 (with 94% identity on ≥88% of its length for all of them) and bacteriophage Dev2 infecting *Cronobacter turicensis* (with 83% identity on 85% of its length) (34). Alignment of these related bacteriophages with LM33_P1 revealed a similar spatial genome organization and confirmed the high homology between them (data not shown). Strikingly, the 5' extremity (the first 650 nucleotides) of the tail fiber gene is highly conserved in each bacteriophage genome, while the remaining part is highly divergent. The corresponding N-terminal region (IPR005604/PF03906, InterPro/Pfam database) of this tail fiber protein is involved in its connection to the tail-tube (35) while the C-terminal part, involved in host recognition, often carries hydrolase activities as the endosialidase of bacteriophage K F used for exopolysaccharide degradation (33, 36). BLAST searches on the C-terminal part of the tail fiber of bacteriophage LM33_P1 revealed homology to a domain belonging to the pectin lyase superfamily (IPR011050). Tridimensional structure prediction using Phyre$^2$ database (37) confirmed its close proximity to the endopolygalacturonase of *Erwinia carotovora* that belongs to the pectin lyase superfamily (100% amino-acid predicted with a confidence >90% for the tertiary structure, index of confidence for homologous protein 94.1%, Protein Data Bank entry: 1BHE).

Bacteriophage LM33_P1 is Highly Efficient and Rapid In Vitro.

Adsorption of LM33_P1 bacteriophage on its host is fast with ≥90% of the viral population attached to cells after 3.5 minutes with an adsorption constant of $1.2 \times 10^8$ mL/min. Newly produced virions are detected within the bacteria as soon as 7 minutes post-infection (eclipse period) while host lysis occurs in 9 minutes (latent period) with a burst size of 317 (95% confidence interval: 289-345) (data not shown).

In liquid medium, when LM33_P1 was mixed with its host, the absorbance value of LM33 cells started to decline (sign of lysis) within 15 minutes (MOI of 1). With much fewer bacteriophages (MOI of $10^{-6}$) lysis still occurred within 60 minutes. On solid medium, LM33_P1 forms clear and large plaques, whose diameter increases rapidly overtime with a visible halo around clear areas. This halo suggests the presence of a diffusible enzyme that most likely carries a depolymerase activity (38).

Bacteriophage LM33_P1 Specifically Binds to O25b LPS O-Antigen.

Host range of bacteriophage LM33_P1 strongly suggested that O-chain of LPS could be involved in its specificity. Using LPS competition assays we observed that purified LPS from strain LM33 was able to partially inhibit interaction between bacteriophage LM33_P1 and strain LM33 as well as other O25b strains (Table 2).

First, we demonstrated that purified LPS reduced the number of plaque-forming units when mixed with bacteriophages before application on a bacterial layer (mean reduction of 1.0±0.23 $Log_{10}$ from 15 assays with five different O25b strains). Together with the reduction of the number of plaques, we observed a reduction of plaque diameters suggesting that LPS molecules prevented newly released bacteriophages to infect surrounding hosts (FIG. 1). These observations are specific of bacteriophage LM33_P1 interaction with O25b strains since: i) O25b LPS extract from strain LM33 was not able to affect interaction of other bacteriophages targeting non O25b strains and ii) LPS extract from non O25b strains (O25a, O6 and O17) was unable to alter interaction between bacteriophage LM33_P1 and strain LM33 (Table 2).

Second, LPS extract from O25b strain (LM33) was also reducing infectivity of bacteriophage LM33_P1 on liquid medium in a dose dependent manner (data not shown), while LPS extracts from O6 and O25a strains had no effect.

Third, using an O-type specific antibody to aggregate O25 strains for serotyping, we found that bacteriophage LM33_P1 prevented aggregation of strain LM33 (data not shown).

Fourth, using the E. coli O25b 81009 and its isogenic rough derivative (LPS deficient strain obtained by deleting the gene encoding for the O-antigen ligase) (21) we observed that bacteriophage LM33_P1 infects the wild type strain 81009 while the LPS deficient strain is resistant. Conversely, we confirmed that bacteriophage LM33_P1 could not adsorb on the LPS defective strain.

Adsorption of Bacteriophage LM33_P1 is Hindered by Capsule Production.

Production of exopolysaccharides is a well-known bacteriophage resistance mechanism and might be involved in the non-adsorption of bacteriophage LM33_P1 observed in five randomly chosen LM33_P1 resistant strains (81009 WT, JJ1886, S242, B-1, C-1). Since, in some cases (type II capsule), the synthesis of exopolysaccharides is temperature dependent, we investigated LM33_P1 susceptibility on all O25b resistant strains (n=36) at 20° C. We observed that nine of them (25%) became susceptible at this temperature (data not shown).

Bacteriophage LM33_P1 Efficiently Infects its Host In Vivo.

As bacteriophage LM33_P1 exhibited impressive in vitro characteristics, we investigated its in vivo activity in three different animal infection models relevant to ST131 clinical epidemiology: pneumonia, septicemia and urinary tract infection (FIGS. 2-4). Since strain LM33 was isolated from a patient with pneumonia, we first attempted to establish pneumonia in mice. Using an inoculum 50 times higher than previously reported in such model (30) and despite clear macroscopic lung lesions, strain LM33 was not lethal preventing us to use survival as an indicator of bacteriophage efficacy. We therefore evaluated LM33_P1 efficacy by counting bacteria from lung homogenates collected 17 hours following infection. Three groups of mice were treated 4 hours post-infection either by control solution (PBS), intranasal (MOI 50) or intraperitoneal (MOI 500) bacteriophages. Independently of the administration route, we observed a 3 $Log_{10}$ reduction in bacterial load when mice received bacteriophage treatments compared to control group (PBS-treated animal: $5.4\times10^7$ cfu/g, intranasally LM33_P1-treated: $2.7\times10^4$ cfu/g, intraperitoneally LM33_P1-treated: $3.3\times10^4$ cfu/g, p<0.01). Interestingly, the number of bacteriophages in the lung tissue was similar between intranasally and intraperitoneally-treated mice despite the latter had received 10 times higher dose.

Then, we challenged the fast in vitro kinetics parameters of bacteriophage LM33_P1 in a murine model of septicemia previously reported (6, 7) using the H1659 ST131-O25b:H4 strain (6) (strain LM33 was not lethal in this model), on which LM33_P1 is as efficient as on strain LM33 (EOP=1). Following a subcutaneous inoculation of $1\times10^9$ cfu, septic metastasis in several organs were rapidly observed (first deaths occurred in less than 24 hours). Intraperitoneal administrations of bacteriophage LM33_P1 (MOI 60, single dose at H2 post-infection or two doses at H2 and H12 post-infection) were not sufficient to prevent animals death. However, in a subset of animals that died within the same time interval (between 24 and 30 hours), bacteria and bacteriophages content was analyzed: i) in liver, spleen and lung-heart homogenates of bacteriophage-treated groups the number of bacteria was reduced compared to control group;

ii) two doses appeared to be more efficient than a single one, reaching a significant reduction of approximately 1.4 $Log_{10}$ (median bacterial count decrease from $8.5\times10^6$ to $2.9\times10^5$ in heart-lungs, $7.7\times10^5$ to $3.2\times10^4$ in the liver and $3.5\times10^5$ to $1.4\times10^4$ cfu/g in the spleen); iii) bacteriophage counts were in the same order of magnitude in all organs, but were significantly higher when two doses were administered ($2.0\times10^{10}$ vs $4.0\times10^9$ pfu/g, p<0.01); iv) the amount of bacteriophages was 3 to 6 $Log_{10}$ higher than the amount of the bacteria in each mouse for all organs. All of these observations revealed that bacteriophage LM33_P1 was able to infect strain H1659 in each organ considered.

Finally, as E. coli is a major pathogen in UTIs, we assessed bacteriophage LM33_P1 efficacy in a murine UTI model. Twenty-four hours following intra-urethral injection of $5.10^7$ cfu of strain LM33, mice received a single bacteriophage treatment intraperitoneally (MOI of 200). Forty-eight hours post-infection, a 2 $Log_{10}$ reduction of the bacterial load was observed in the kidneys in the treated group compared to control ($1.5\times10^5$ vs $8.8\times10^2$ cfu/g, p<0.001).

Altogether these data firmly demonstrate the ability of bacteriophage LM33_P1 in infecting O25b strains in vivo.

Discussion:

Antibiotic resistance is a public health problem worldwide. In less than 10 years, multi-drug resistant ST131-O25b:H4 E. coli clonal complex have spread over the planet, now being present in both animals and humans (2). Unfortunately, the discovery of new antibiotics did not turn out to be as successful as initially expected, leading to the reappraisal of phage therapy. One of the main advantages of bacteriophages often reported is their specificity to infect few strains within a species, having then a limited impact on patient's microbiota. Along with monoclonal antibodies (anti-O25b antibodies have been proven to exert a protective effect in mouse septicemia model) (39), bacteriophages are the only anti-infectious tools that could reach such specificity.

Using an ST131-O25b:H4 clinical isolate of E. coli (strain LM33), we isolated a bacteriophage, LM33_P1, which was found to be extremely specific. Extensive tests on almost 300 strains belonging to various serotypes revealed that this bacteriophage infects exclusively O25b strains. Interestingly, O25b O-antigen is present in the archetypal ST131 clonal complex but also in ST69, another antibiotic resistant spreading clone of E. coli, the "clonal group A" (11, 40). In a therapeutic projection and based on the pandemic lineages of extraintestinal pathogenic E. coli (41), we observed a greater susceptibility among both of these STs (70%) compared to less antibiotic resistant O25b STs like ST95 and minor ones (23%).

Additionally, the majority of strains belonging to the ST131 clonal complex displays an O25b O-antigen while a minor part, less resistant to antibiotics, displays an O16 serogroup (42). Bacteriophage LM33_P1 specificity was linked to the O25b O-antigen and not to the sequence type (i.e. none of the non-O25b ST131 strains were susceptible to bacteriophage LM33_P1 while all O25b-ST69 strains tested were susceptible). Furthermore, susceptibility of ST131-O25b:H4 strains to bacteriophage LM33_P1 was independent of the fimH allele, a marker of the epidemiologic evolution of this clone (32). Besides, bacteriophage LM33_P1 was unable to infect O25a strains, despite a highly similar O-antigen structure where polysaccharides repeated units only differ by one monosaccharide (fucose versus rhamnose), a fine discrimination that is not possible with classical antibodies used for serotyping until the recent description of O25b monoclonal antibodies (21).

Our investigations led to estimate that global host coverage of bacteriophage LM33_P1 on O25b strains is 64%. We consider that this coverage is reliable as we first avoided sampling bias by screening a large collection (may be one of the largest ever tested for such study) obtained from different sources with many serotypes. Second, we assessed strain susceptibility in a rigorous way using EOP determination that excludes atypical results and false positive like lysis from without (43, 44). Finally, 90% of EOP values were within −1.5 and 1.5 $Log_{10}$ units, which indicate that strains infected with a very low efficiency are infrequent. In addition to this specialized host range, we found that bacteriophage LM33_P1 possesses optimized properties to infect its host. Compared to data available in the literature, we found that it is the quickest T7-like bacteriophage ever reported, lysing its host within 10 minutes while T7 takes 13 to 16 minutes (45, 46). Part of this success relies on its absorption constant ($1.2 \times 10^8$ mL/min) which was found 10 times higher that most of bacteriophages (47-50) and its burst size that is also on the top half of values usually observed (51).

To prevent phage adsorption bacteria can mask phage receptors by the production of extracellular exopolysaccharides (capsules), which can also help bacteria escaping immune cells recognition (52, 53). We found that 25% of strains reversed their phenotype towards bacteriophage LM33_P1 from resistant to susceptible, when tested at 20° C., a temperature known to turn off type II capsule production (24). Therefore, bacteriophage LM33_P1 coverage increased to 80% among all ST131-O25b:H4 strains and to 73% among all O25b strains tested. It was also previously shown that bacteriophages can defeat this defense mechanism using tail fibers that possess depolymerase activities (54-57) and we can reasonably assume that isolation of LM33_P1 variants or different bacteriophages could provide such solution to improve (by synergy) the coverage rate of O25b strains (56, 58, 59).

With the goal of using bacteriophages to treat human bacterial infections, the translation from in vitro activity (forming plaques) to in vivo efficacy (curing a disease) is not guaranteed, despite high success rate (60). Our investigation of the in vivo curative potential of bacteriophage LM33_P1 revealed indeed that, in the three models tested, this bacteriophage was able to infect targeted bacteria in several body compartments and via different administration routes. These treatments were not optimized to reach maximum efficacy as many parameters would need to be evaluated, which require dedicated studies out of the focus of this work. Indeed, bacteriophages pharmacokinetic is highly complex, due to their intrinsic properties (bacteria-driven self-expansion, diffusion, adsorption, threshold to prime a viral expansion, etc.) (61-63) and cannot be compared to traditional pharmacokinetic of antibiotics. In addition, in such experimental models, the curative dose applied is always related to the initial known dose of pathogenic bacteria, which is therefore a gross estimation of what is needed (amount of bacteria could be highly different between time of inoculation and treatment due to bacterial growth). Consequently, our data should not be over-translated to the clinical setting. Nevertheless, it remains indisputable that bacteriophages, including LM33_P1 as shown in this study, can quickly reduce the load of their host within a complex environment including the gut of mammals (64). Our data also support higher efficacy when bacteriophages are applied locally (intranasal instillation to treat pneumonia) than when used via a systemic administration. In a therapeutic approach, such bacteriophages could be used as a selective antimicrobial agent for controlling passive carriage of ST131-O25b:H4 strains in human gut in order to reduce its dissemination, particularly in healthcare-associated environments. Indeed, E. coli strains residing in the digestive tract constitute a well-known reservoir for urinary tract infections but probably also for ventilator-associated pneumonia (14). Finally, as no positive correlation between antibiotic and bacteriophage resistance has ever been shown, phage therapy remains a valuable resource to control such multi-drug resistant pathogens. Clinical trials are now required and are indeed encouraged by the recent position taken by the European Medicine Agency (65), in order to better define to which extent promises of bacteriophages, such as the one reported here, can be translated into efficient treatment.

Beside the classical phage therapy approach, bacteriophage LM33_P1 or proteins from it offer opportunities to develop several tools. The tail fiber could be used to kill specifically O25b E. coli strains using bacteriocins, as previously shown for O104 E. coli strains involved in enterohemorragic colitis (66). Other approaches could be foreseen where bacteriophages are reprogrammed and could suppress antibiotic resistance genes using CRISPR-Cas system (67) or express well-chosen beneficial enzymes to fight biofilm (68). Deeper investigations on the infectious cycle of this bacteriophage are now required to determine which molecular mechanisms are responsible for its fast-killing component. Bacteriophage LM33_P1 could also be used from now as a starting platform to develop highly virulent synthetic bacteriophages with various host specificity (69).

TABLE 1

Main genotypic characteristics of strain LM33 and plasmid pLM33.

Strain LM33 chromosome (accession number: PRJEB9970)

General informations

| | | |
|---|---|---|
| Genome size: 5 450 287 bp | GC content: 51.5% | Number of genes: 5276 |
| Sequence type: ST131 | Serotype: O25b:H4 | Phylogroup: B2 |
| (according to the Achtman scheme) | | fimH allele: 22 |

Genes coding for virulence factors*

| | |
|---|---|
| iss (increased serum survival) | aer (aerotaxis sensor receptor) |
| iroN (Enterobactin siderophore receptor protein) | fyuA (siderophore) |
| prfB (P-related fimbriae regulatory gene) | papC (P fimbriae) |
| traT (serum resistance-associated outer membrane protein) | papGIII (P fimbriae) |
| gad (glutamate decarboxylase) | mchF (ABC transporter protein) |

Genes coding for antibiotic resistance*

Aminoglycoside resistance: strB, aacA4, strA, aac(6')-IIc
Beta-lactam resistance: blaDHA-7, blaSHV-12, blaTEM-1C
Quinolone resistance: aac(6')Ib-cr, qnrB4
MLS resistance: ere(A)
Sulphonamide: sul1; thrimethoprim: dfrA18

Plasmid pLM33 (accession number: PRJEB9970)

General informations

| | | |
|---|---|---|
| Plasmid size: 296 909 bp | GC content: 47.2% | Number of genes: 382 |
| Incompatibility group: H | | |

Genes coding for virulence factors* none

TABLE 1-continued

Main genotypic characteristics of strain LM33 and plasmid pLM33.

Genes coding for antibiotic resistance*

Aminoglycoside resistance: strA, strB, aacA4, aac(6')-IIc
Beta-lactam resistance: blaSHV-12, blaTEM-1C
Quinolone resistance: aac(6')Ib-cr
MLS resistance: ere(A)

*data obtained using the center for genetic epidemiology server (70, 71)

TABLE 2

Data obtained during plaque test inhibition assays with different LPS extracts and randomly chosen couples of viruses-bacteria.

| | | Inhibitory effect of various LPS extracts | | | |
|---|---|---|---|---|---|
| | Interaction tested | | | | |
| Bacteriophage | Bacteria (serotype) | O25b (LM33) | O6 (536) | O17 (LM02) | O25a (ECOR51) |
| LM33_P1 | LM33 (O25b) | (+) | (−) | (−) | (−) |
| " | LM34 (O25b) | (+) | (−) | (−) | (−) |
| " | LM36 (O25b) | (+) | (−) | (−) | (−) |
| " | AVC02 (O25b) | (+) | (−) | (−) | (−) |
| " | AVC03(O25b) | (+) | (−) | (−) | (−) |
| 536_P1[a] | 536 (O6) | (−) | (−) | — | — |
| 423_P1[b] | H17 (O16) | (−) | — | — | — |
| 416_P1[b] | LM49 (O2b) | (−) | — | — | — |
| LF82_P2[c] | LF82 (O83) | (−) | — | — | — |
| LF82_P2[c] | RY09 (O4) | (−) | — | — | — |

(+)/(−): presence/absence of an inhibitory effect of LPS extract,
—: not tested.
[a]described in (30),
[b]bacteriophages isolated using ventilator-associated pneumonia (VAP) strains (423, 416) and active on others VAP strains (H17, LM49),
[c]bacteriophage isolated using an adherent-invasive E. coli (LF82) and active on VAP strain RY09.

REFERENCES

Throughout this application, various references describe the state of the art to which this invention pertains. The disclosures of these references are hereby incorporated by reference into the present disclosure.

1. Tenaillon O, Skurnik D, Picard B, & Denamur E (2010) The population genetics of commensal Escherichia coli. Nat Rev Microbiol. 8(3):207-217. doi: 210.1038/nrmicro2298.
2. Nicolas-Chanoine M H, Bertrand X, & Madec J Y (2014) Escherichia coli ST131, an Intriguing Clonal Group. Clin Microbiol Rev. 27(3):543-574.
3. Rogers B A, Sidjabat H E, & Paterson D L (2011) Escherichia coli O25b-ST131: a pandemic, multiresistant, community-associated strain. J Antimicrob Chemother. 66(1):1-14. doi: 10.1093/jac/dkq1415. Epub 210 November 1016.
4. Russo T A & Johnson J R (2000) Proposal for a new inclusive designation for extraintestinal pathogenic isolates of Escherichia coli: ExPEC. J Infect Dis. 181(5): 1753-1754. Epub 2000 May 1715.
5. Picard B, et al. (1999) The link between phylogeny and virulence in Escherichia coli extraintestinal infection. Infect Immun. 67(2):546-553.
6. Mora A, et al. (2014) Virulence patterns in a murine sepsis model of ST131 Escherichia coli clinical isolates belonging to serotypes O25b:H4 and O16:H5 are associated to specific virotypes. PLoS One. 9(1):e87025. doi: 87010.81371/journal.pone.0087025. eCollection 0082014.
7. Johnson J R, Porter S B, Zhanel G, Kuskowski M A, & Denamur E (2012) Virulence of Escherichia coli clinical isolates in a murine sepsis model in relation to sequence type ST131 status, fluoroquinolone resistance, and virulence genotype. Infect Immun. 80(4):1554-1562. doi: 1510.1128/IAI.06388-06311. Epub 0212 February 06386.
8. Peirano G, et al. (2014) Global incidence of carbapenemase-producing Escherichia coli ST131. Emerg Infect Dis 20(11): 1928-1931.
9. Coque T M, et al. (2008) Dissemination of clonally related Escherichia coli strains expressing extended-spectrum beta-lactamase CTX-M-15. Emerg Infect Dis. 14(2):195-200. doi: 110.3201/eid1402.070350.
10. Nicolas-Chanoine M H, et al. (2008) Intercontinental emergence of Escherichia coli clone O25:H4-ST131 producing CTX-M-15. J Antimicrob Chemother. 61(2):273-281. Epub 27 Dec. 2011.
11. Colomer-Lluch M, et al. (2013) Detection of quinolone-resistant Escherichia coli isolates belonging to clonal groups O25b:H4-B2-ST131 and O25b:H4-D-ST69 in raw sewage and river water in Barcelona, Spain. J Antimicrob Chemother 68(4):758-765.
12. Reardon S (2014) Phage therapy gets revitalized. Nature 510(7503):15-16.
13. Lefort A, et al. (2011) Host factors and portal of entry outweigh bacterial determinants to predict the severity of Escherichia coli bacteremia. J Clin Microbiol. 49(3):777-783. doi: 710.1128/JCM.01902-01910. Epub 0210 December 01922.
14. Messika J, et al. (2012) Pathophysiology of Escherichia coli ventilator-associated pneumonia: implication of highly virulent extraintestinal pathogenic strains. Intensive Care Med 38(12):2007-2016.
15. Smati M, et al. (2013) Real-time PCR for quantitative analysis of human commensal Escherichia coli populations reveals a high frequency of subdominant phylogroups. Appl Environ Microbiol. 79(16):5005-5012. doi: 5010.1128/AEM.01423-01413. Epub 0213 June 01414.
16. Ochman H & Selander R K (1984) Standard reference strains of Escherichia coli from natural populations. J Bacteriol. 157(2):690-693.
17. Clermont O, Christenson J K, Denamur E, & Gordon D M (2013) The Clermont Escherichia coli phylo-typing method revisited: improvement of specificity and detection of new phylo-groups. Environ Microbiol Rep. 5(1): 58-65. doi: 10.1111/1758-2229.12019. Epub 1212 December 12024.
18. Clermont O, Gordon D, & Denamur E (2015) A guide to the various phylogenetic classification schemes for Escherichia coli and the correspondence among schemes. Microbiology 161 (Pt 5):980-988.
19. Clermont O, Johnson J R, Menard M, & Denamur E (2007) Determination of Escherichia coli O types by allele-specific polymerase chain reaction: application to the O types involved in human septicemia. Diagn Microbiol Infect Dis. 57(2):129-136. Epub 26 Oct. 2003.
20. Clermont O, et al. (2011) Animal and human pathogenic Escherichia coli strains share common genetic backgrounds. Infect Genet Evol. 11(3):654-662. doi: 610.1016/j.meegid.2011.1002.1005. Epub 211 February 1013.
21. Szijarto V, et al. (2014) Diagnostic potential of monoclonal antibodies specific to the unique O-antigen of multidrug-resistant epidemic Escherichia coli clone ST131-O25b:H4. Clin Vaccine Immunol. 21(7):930-939. doi: 910.1128/CVI.00685-00613. Epub 0214 April 00630.

22. Boulanger P (2009) Purification of bacteriophages and SDS-PAGE analysis of phage structural proteins from ghost particles. Methods Mol Biol 502:227-238.
23. Saussereau E, et al. (2014) Effectiveness of bacteriophages in the sputum of cystic fibrosis patients. Clin Microbiol Infect. 20(12):0983-990. doi: 910.1111/1469-0691.12712. Epub 1214 July 12726.
24. Whitfield C (2006) Biosynthesis and assembly of capsular polysaccharides in *Escherichia coli*. Annu Rev Biochem 75:39-68.
25. Davis M R, Jr. & Goldberg J B (2012) Purification and visualization of lipopolysaccharide from Gram-negative bacteria by hot aqueous-phenol extraction. J Vis Exp. (63).(pii):3916. doi: 3910.3791/3916.
26. Hyman P & Abedon S T (2009) Practical methods for determining phage growth parameters. Methods Mol Biol. 501:175-202.(doi):10.1007/1978-1001-60327-60164-60326_60318.
27. Pickard D J (2009) Preparation of bacteriophage lysates and pure DNA. Methods Mol Biol. 502:3-9.(doi): 10.1007/1978-1001-60327-60565-60321_60321.
28. Aziz R K, et al. (2008) The RAST Server: rapid annotations using subsystems technology. BMC Genomics 9:75.
29. Vallenet D, et al. (2013) MicroScope—an integrated microbial resource for the curation and comparative analysis of genomic and metabolic data. Nucleic Acids Res 41 (Database issue):D636-647.
30. Dufour N, Debarbieux L, Fromentin M, & Ricard J D (2015) Treatment of Highly Virulent Extraintestinal Pathogenic *Escherichia coli* Pneumonia With Bacteriophages. Crit Care Med 43(6):e190-198.
31. Vimont S, et al. (2012) The CTX-M-15-producing *Escherichia coli* clone O25b: H4-ST131 has high intestine colonization and urinary tract infection abilities. PLoS One 7(9):e46547.
32. Johnson J R, et al. (2013) Abrupt emergence of a single dominant multidrug-resistant strain of *Escherichia coli*. J Infect Dis 207(6):919-928.
33. Scholl D & Merril C (2005) The genome of bacteriophage K1F, a T7-like phage that has acquired the ability to replicate on K strains of *Escherichia coli*. J Bacteriol 187(24):8499-8503.
34. Kajsik M, et al. (2014) Characterization and genome sequence of Dev2, a new T7-like bacteriophage infecting *Cronobacter turicensis*. Arch Virol 159(11):3013-3019.
35. Steven A C, et al. (1988) Molecular substructure of a viral receptor-recognition protein. The gp 17 tail-fiber of bacteriophage T7. J Mol Biol 200(2):351-365.
36. Casjens S R & Molineux U (2012) Short noncontractile tail machines: adsorption and DNA delivery by podoviruses. Adv Exp Med Biol 726:143-179.
37. Kelley L A, Mezulis S, Yates C M, Wass M N, & Sternberg M J (2015) The Phyre2 web portal for protein modeling, prediction and analysis. Nat Protoc 10(6):845-858.
38. Adams M H & Park B H (1956) An enzyme produced by a phage-host cell system. II. The properties of the polysaccharide depolymerase. Virology 2(6):719-736.
39. Szijarto V, et al. (2015) Bactericidal monoclonal antibodies specific to the lipopolysaccharide O antigen from multidrug-resistant *Escherichia coli* clone ST131-O25b: H4 elicit protection in mice. Antimicrob Agents Chemother 59(6):3109-3116.
40. Manges A R, et al. (2001) Widespread distribution of urinary tract infections caused by a multidrug-resistant *Escherichia coli* clonal group. N Engl J Med 345(14): 1007-1013.
41. Riley L W (2014) Pandemic lineages of extraintestinal pathogenic *Escherichia coli*. Clin Microbiol Infect 20(5): 380-390.
42. Johnson J R, et al. (2014) Rapid and specific detection, molecular epidemiology, and experimental virulence of the 016 subgroup within *Escherichia coli* sequence type 131. J Clin Microbiol 52(5):1358-1365.
43. Khan Mirzaei M & Nilsson A S (2015) Isolation of phages for phage therapy: a comparison of spot tests and efficiency of plating analyses for determination of host range and efficacy. PLoS One 10(3):e0118557.
44. Abedon S T (2011) Lysis from without. Bacteriophage. 1(1):46-49.
45. Heineman R H & Bull J J (2007) Testing optimality with experimental evolution: lysis time in a bacteriophage. Evolution 61(7): 1695-1709.
46. Nguyen H M & Kang C (2014) Lysis delay and burst shrinkage of coliphage T7 by deletion of terminator Tphi reversed by deletion of early genes. J Virol 88(4):2107-2115.
47. Bayer M E (1968) Adsorption of bacteriophages to adhesions between wall and membrane of *Escherichia coli*. J Virol 2(4):346-356.
48. Olkkonen V M & Bamford D H (1989) Quantitation of the adsorption and penetration stages of bacteriophage phi 6 infection. Virology 171(1):229-238.
49. Puck T T, Garen A, & Cline J (1951) The mechanism of virus attachment to host cells. I. The role of ions in the primary reaction. J Exp Med 93(1):65-88.
50. Storms Z J, Smith L, Sauvageau D, & Cooper D G (2012) Modeling bacteriophage attachment using adsorption efficiency. Biochemical Engineering Journal 64:22-29.
51. De Paepe M & Taddei F (2006) Viruses' life history: towards a mechanistic basis of a trade-off between survival and reproduction among phages. PLoS Biol 4(7): e193.
52. Labrie S J, Samson J E, & Moineau S (2010) Bacteriophage resistance mechanisms. Nat Rev Microbiol 8(5): 317-327.
53. Jann K & Jann B (1987) Polysaccharide antigens of *Escherichia coli*. Rev Infect Dis 9 Suppl 5:S517-526.
54. Bull J J, Vimr E R, & Molineux U (2010) A tale of tails: Sialidase is key to success in a model of phage therapy against K1-capsulated *Escherichia coli*. Virology 398(1): 79-86.
55. Hughes K A, Sutherland I W, Clark J, & Jones M V (1998) Bacteriophage and associated polysaccharide depolymerases—novel tools for study of bacterial biofilms. J Appl Microbiol 85(3):583-590.
56. Lin T L, et al. (2014) Isolation of a bacteriophage and its depolymerase specific for K1 capsule of *Klebsiella pneumoniae*: implication in typing and treatment. J Infect Dis 210(11):1734-1744.
57. Mushtaq N, Redpath M B, Luzio J P, & Taylor P W (2005) Treatment of experimental *Escherichia coli* infection with recombinant bacteriophage-derived capsule depolymerase. J Antimicrob Chemother 56(1): 160-165.
58. Born Y, et al. (2014) The tail-associated depolymerase of *Erwinia amylovora* phage L1 mediates host cell adsorption and enzymatic capsule removal, which can enhance infection by other phage. Environ Microbiol 16(7):2168-2180.

59. Schmerer M, Molineux IJ, & Bull J J (2014) Synergy as a rationale for phage therapy using phage cocktails. PeerJ 2:e590.
60. Henry M, Lavigne R, & Debarbieux L (2013) Predicting in vivo efficacy to guide the choice of therapeutic bacteriophages to treat pulmonary infections. Antimicrob Agents Chemother.
61. Cairns B J, Timms A R, Jansen V A, Connerton I F, & Payne R J (2009) Quantitative models of in vitro bacteriophage-host dynamics and their application to phage therapy. PLoS Pathog 5(1):e1000253.
62. Payne R J & Jansen V A (2001) Understanding bacteriophage therapy as a density-dependent kinetic process. J Theor Biol 208(1):37-48.
63. Weld R J, Butts C, & Heinemann J A (2004) Models of phage growth and their applicability to phage therapy. J Theor Biol 227(1): 1-11.
64. *Maura* D, et al. (2012) Intestinal colonization by enteroaggregative *Escherichia coli* supports long-term bacteriophage replication in mice. Environ Microbiol. 14(8): 1844-1854. doi: 1810.1111/j.1462-2920.2011.02644.x. Epub 0211 November 02628.
65. European Medicines Agency (2015) Workshop on the therapeutic use of bacteriophages.
66. Scholl D, Gebhart D, Williams S R, Bates A, & Mandrell R (2012) Genome sequence of *E. coli* O104:H4 leads to rapid development of a targeted antimicrobial agent against this emerging pathogen. PLoS One 7(3):e33637.
67. Yosef I, Manor M, Kiro R, & Qimron U (2015) Temperate and lytic bacteriophages programmed to sensitize and kill antibiotic-resistant bacteria. Proc Natl Acad Sci USA 112(23):7267-7272.
68. Lu T K & Collins J J (2007) Dispersing biofilms with engineered enzymatic bacteriophage. Proc Natl Acad Sci USA 104(27):11197-11202.
69. Ando H, Lemire S, Pires D P, & Lu T K (2015) Engineering Modular Viral Scaffolds for Targeted Bacterial Population Editing. Cell Systems 1(3): 187-196.
70. Joensen K G, et al. (2014) Real-time whole-genome sequencing for routine typing, surveillance, and outbreak detection of verotoxigenic *Escherichia coli*. J Clin Microbiol 52(5):1501-1510.
71. Zankari E, et al. (2012) Identification of acquired antimicrobial resistance genes. J Antimicrob Chemother 67(11):2640-2644.

The invention claimed is:

1. An isolated bacteriophage comprising a polypeptide having an amino acid sequence having at least 95% identity with the amino acid sequence of SEQ ID NO:1 and a genomic sequence having at least 80% of identity with the genomic sequence of LM33-P1 represented by SEQ ID NO: 2, wherein the genomic sequence of the isolated bacteriophage is not the genomic sequence of LM33-P1 represented by SEQ ID NO: 2; wherein the isolated bacteriophage is able to produce a lytic infection in the *Escherichia coli* clone ST131-O25b:H4.

2. The isolated bacteriophage according to claim 1 in lyophilized form.

3. The isolated bacteriophage according to claim 1, wherein the isolated bacteriophage comprises a genomic sequence having at least 90% of identity with the genomic sequence of LM33-P1 represented by SEQ ID NO: 2.

4. The isolated bacteriophage according to claim 3, wherein the isolated bacteriophage comprises a polypeptide having an amino acid sequence having at least 98% identity with the amino acid sequence of SEQ ID NO:1.

5. The isolated bacteriophage according to claim 1, wherein the isolated bacteriophage comprises a genomic sequence having at least 95% of identity with the genomic sequence of LM33-P1 represented by SEQ ID NO: 2.

6. The isolated bacteriophage according to claim 5, wherein the isolated bacteriophage comprises a polypeptide having an amino acid sequence having at least 98% identity with the amino acid sequence of SEQ ID NO:1.

7. An isolated lyophilized bacteriophage comprising a polypeptide having an amino acid sequence having at least 95% identity with the amino acid sequence of SEQ ID NO:1 and a genomic sequence having at least 80% of identity with the genomic sequence of LM33-P1 represented by SEQ ID NO: 2; wherein the isolated bacteriophage is able to produce a lytic infection in the *Escherichia coli* clone ST131-025b:H4.

8. The isolated lyophilized bacteriophage according to claim 7, which is the bacteriophage strain LM33-P1 deposited at the French National Collection of Microorganisms at the Institut Pasteur under Accession Number CNCM I-4964 on Apr. 3, 2015.

9. A method of treating an infection caused by an *Escherichia coli* ST131-O25b:H4 clone in a patient in need thereof comprising administering to the patient a therapeutically effective amount of an isolated bacteriophage comprising a polypeptide having an amino acid sequence having at least 95% identity with the amino acid sequence of SEQ ID NO:1 and a genomic sequence having at least 80% of identity with the genomic sequence of LM33-P1 represented by SEQ ID NO: 2; wherein the isolated bacteriophage is able to produce a lytic infection in the *Escherichia coli* clone ST131-025b:H4.

10. The method of claim 9, wherein the infection is selected from the group consisting of cystic fibrosis, otitis media, keratitis, endophthalmitis, bacteremia, burn wound infection, pneumonia, meningitis, peritonitis, a urinary tract infection, sepsis, nosocomial infection, lung infection, peritonitis, sepsis, and meningitis.

11. The method of claim 9, wherein the genomic sequence of the administered isolated bacteriophage is not the genomic sequence of LM33-P1 represented by SEQ ID NO: 2.

12. The method of claim 11, wherein the infection is selected from the group consisting of cystic fibrosis, otitis media, keratitis, endophthalmitis, bacteremia, burn wound infection, pneumonia, meningitis, peritonitis, a urinary tract infection, sepsis, nosocomial infection, lung infection, peritonitis, sepsis, and meningitis.

13. The method of claim 9, wherein the administered isolated bacteriophage is the bacteriophage strain LM33-P1 deposited at the French National Collection of Microorganisms at the Institut Pasteur under Accession Number CNCM I-4964 on Apr. 3, 2015.

14. The method of claim 13, wherein the infection is selected from the group consisting of cystic fibrosis, otitis media, keratitis, endophthalmitis, bacteremia, burn wound infection, pneumonia, meningitis, peritonitis, a urinary tract infection, sepsis, nosocomial infection, lung infection, peritonitis, sepsis, and meningitis.

15. The method of claim 9, wherein the genomic sequence of the administered isolated bacteriophage comprises a genomic sequence having at least 90% of identity with the genomic sequence of LM33-P1 represented by SEQ ID NO: 2.

16. The method of claim 15, wherein the administered isolated bacteriophage comprises a polypeptide having an amino acid sequence having at least 98% identity with the amino acid sequence of SEQ ID NO:1.

17. The method of claim 9, wherein the genomic sequence of the administered isolated bacteriophage comprises a genomic sequence having at least 95% of identity with the genomic sequence of LM33-P1 represented by SEQ ID NO: 2.

18. The method of claim 17, wherein the administered isolated bacteriophage comprises a polypeptide having an amino acid sequence having at least 98% identity with the amino acid sequence of SEQ ID NO:1.

19. The method of claim 16, wherein the infection is selected from the group consisting of cystic fibrosis, otitis media, keratitis, endophthalmitis, bacteremia, burn wound infection, pneumonia, meningitis, peritonitis, a urinary tract infection, sepsis, nosocomial infection, lung infection, peritonitis, sepsis, and meningitis.

20. The method of claim 18, wherein the infection is selected from the group consisting of cystic fibrosis, otitis media, keratitis, endophthalmitis, bacteremia, burn wound infection, pneumonia, meningitis, peritonitis, a urinary tract infection, sepsis, nosocomial infection, lung infection, peritonitis, sepsis, and meningitis.

* * * * *

SEQUENCE LISTING

```
<160> NUMBER OF SEQ ID NOS: 2

<210> SEQ ID NO 1
<211> LENGTH: 726
<212> TYPE: PRT
<213> ORGANISM: Artificial Sequence
<220> FEATURE:
<223> OTHER INFORMATION: Synthetic bacteriophage tail fiber

<400> SEQUENCE: 1

Met Ser Thr Ile Thr Gln Phe Pro Ser Gly Asn Thr Gln Tyr Arg Ile
1               5                   10                  15

Glu Phe Asp Tyr Leu Ala Arg Thr Phe Val Val Thr Leu Val Asn
            20                  25                  30

Ser Ser Asn Pro Thr Leu Asn Arg Val Leu Glu Val Gly Arg Asp Tyr
        35                  40                  45

Arg Phe Leu Asn Pro Thr Met Ile Glu Met Leu Ala Asp Gln Ser Gly
    50                  55                  60

Phe Asp Ile Val Arg Ile His Arg Gln Thr Gly Thr Asp Leu Val Val
65                  70                  75                  80

Asp Phe Arg Asn Gly Ser Val Leu Thr Ala Ser Asp Leu Thr Asn Ser
                85                  90                  95

Glu Leu Gln Ala Ile His Ile Ala Glu Glu Gly Arg Asp Gln Thr Val
            100                 105                 110

Asp Leu Ala Lys Glu Tyr Ala Asp Ala Ala Gly Ser Ser Ala Gly Asn
        115                 120                 125

Ala Lys Asp Ser Glu Asp Glu Ser Arg Arg Ile Ala Ala Ser Ile Lys
    130                 135                 140

Ala Ala Gly Lys Ile Gly Tyr Ile Thr Arg Arg Ser Phe Glu Lys Gly
145                 150                 155                 160

Phe Asn Val Thr Thr Trp Asn Glu Val Leu Leu Trp Glu Glu Asp Gly
                165                 170                 175

Asp Tyr Tyr Arg Trp Asp Gly Thr Leu Pro Lys Asn Val Pro Ala Gly
            180                 185                 190

Ser Thr Pro Glu Ser Ser Gly Gly Ile Gly Leu Ser Ala Trp Val Ser
        195                 200                 205
```

-continued

Val Gly Asp Ala Ser Leu Arg Ala Asn Leu Ala Asp Ser Asp Gly Ala
    210                 215                 220

Lys Tyr Ile Gly Ser Gly Glu Arg Thr Leu Leu Glu His Asn Asn Asp
225                 230                 235                 240

Val Leu His Ser Lys Asp Phe Pro Thr Leu Gln Ala Ala Ile Asp Ala
                245                 250                 255

Ser Leu Gln Lys Asn Asp Leu Leu Val Ser Pro Gly Asn Tyr Thr Glu
            260                 265                 270

Lys Val Thr Ile Gly Asn Ala Gln Leu Lys Gly Val Gly Gly Ala Thr
        275                 280                 285

Val Leu Lys Thr Pro Ala Asp Phe Thr Asn Thr Val Gln Val Asn Leu
    290                 295                 300

Ala Thr Pro His Trp Gln Phe Arg His Ser Gly Gly Phe Ala Ile Asp
305                 310                 315                 320

Gly Ser Gly Thr Thr Gly Ala Val Gly Ile Ser Phe Asp Pro Ser Asp
                325                 330                 335

Gln Tyr Ser Gly Arg His Asn Phe Ser Asp Val Tyr Ile His Asn Ile
            340                 345                 350

Asn Lys Ala Ile Gln Lys Pro Ser Gly Asn Ile Gly Asn Thr Trp Arg
        355                 360                 365

Asn Ile Gly Ile Ser Thr Cys Asp Trp Gly Tyr Tyr Ala Ile Ser Gly
    370                 375                 380

Ser Glu Met His Cys Gly Ala Asp Thr Leu Tyr Asn Ile His Phe Asp
385                 390                 395                 400

Gly Ile Ser Thr Tyr Ala Val Tyr Leu Asp Gly Thr Val Asp Asn Gly
                405                 410                 415

Gly Gly Gly Ala Trp Trp Leu Lys Asp Ser Ile Ile Glu Ala Ser Gly
            420                 425                 430

Gly Gly Gly Ile Tyr Leu Lys Ser Lys Ser Gly Asp Cys Pro Thr Ser
        435                 440                 445

Pro Cys Gly Val Ser Asn Ile Trp Met Glu Ala Ile Ala Thr Ser Pro
    450                 455                 460

Ala Val Gln Val Asp Gly Val Ala Gln Lys Pro Arg Val Leu Lys Leu
465                 470                 475                 480

Val Asp Thr Ala Ile Phe Phe Ala Glu Tyr Ser Tyr Leu Asn Asn Ile
                485                 490                 495

Glu Leu Ser Asn Ser Asn Leu Val Thr Tyr Gly Cys Arg Phe Asp Asn
            500                 505                 510

Ala Asp Gly Asn Gln Asp Ile Val Val Asp Ala Gln Ser Thr Ile Val
        515                 520                 525

Ala His Asp Val Tyr Leu Asn Gly Ser Ser Gly Lys Asp Val Ile Val
    530                 535                 540

Glu Ser Val Ala Ser Gln Ser Ala Thr Ile Ala Ala Thr Asn Leu Ser
545                 550                 555                 560

Leu Arg Gly Asn Leu Thr Arg Gly Arg Val Phe Asn Thr Pro Thr Gly
                565                 570                 575

Asn Lys Leu Met Ala Ile Thr Phe Asp Ser Gly Ser His Asn Phe Ser
            580                 585                 590

Gly Ser Gly Thr Val Asn Gly Ser Thr Val Ser Asp Gly Leu His Ala
        595                 600                 605

Ala Thr Cys Thr Glu Phe Ser Phe Pro Gly Ala Gly Leu Tyr Glu Met
    610                 615                 620

```
Val Ala Thr Arg Thr Thr Ile Thr Ser Gly Arg Trp Tyr Val Trp Gly
625                 630                 635                 640

Val Asn Ser Arg Leu Gln Ser Gly Ser Ala Asp Ile Ser Ile Thr Ser
            645                 650                 655

Gly Ile Thr Met Gly Ser Val Tyr Thr Lys Pro Gly Glu Trp Ile Ser
        660                 665                 670

Thr Phe Gly Val Gly Lys Ala Ser Thr Thr Gly Thr Val Ala Leu Tyr
    675                 680                 685

Val Ser Thr Gly Gly Gly Ser Gly Ala Thr Val Arg Phe Ser Asp Phe
    690                 695                 700

Phe Ile Ala Glu Phe Thr Thr Gln Ala Gln Ala Leu Ala Phe Ala Asn
705                 710                 715                 720

Ser Arg Met Ser Leu Ser
                725

<210> SEQ ID NO 2
<211> LENGTH: 38979
<212> TYPE: DNA
<213> ORGANISM: Artificial Sequence
<220> FEATURE:
<223> OTHER INFORMATION: Synthetic the genomic sequence of LM33-P1

<400> SEQUENCE: 2
ttcaagaacc tcaagtctcc ccataggccc tctttcagtc cagaccaaag gccctacccg      60
ttactgctcc ttgcagtcac agccagtcta tcataaggtt ggacagatgg tcaagactta     120
aggtcaacga taggctgagg ctatggctta gggaaggacg ataggttggg actattggtc     180
ttctttgagt ctctatctgt ataaccataa gtcacaacca taggtcacag cctacctctc     240
acaaccataa gtcataacct acagtctcac taacctacag tctcaaccat aagcaccaa      300 cacctacagt catagaccta cagttaatag acacaaggct atagacttaa ggtctaagac     360
atgttagtca aagactatat cctcttacac catggggccg acgatagctt aatcaatatt     420
atttcaaatt acctattgac tataggtcca gactatggcc taatagcttc cgtcaacacg     480
acacggcaac aaccggatag tgaagacgcc ggtccggtcc ggttaagtag tcagcctgta     540
agacatacga caacaggca accgacagaa agtagttgac aggcagtaac gacttaaagt      600
aatatgtacc acatcgaaac aacggtgatg accaacactg aatggtctac ctgaagtcct     660
ctgactgaag ggaatgctct ttaacaatct ggataaactc ttaatgtgcg ccgatagcga     720
ctaactacag ggcctttgag tctacatctg aaggccctga ctgatagtca ctaacttaaa     780
ggatggacac tatgaaacac ttaagcacaa tcactaatcg caatgaagta ttcgtgaaca     840
ctaaaggtta tgcgtggatt cagcttaaag agatgacagg agcgcgtcac cgtgtggtag     900
tgcgcaaggt atcaagcaag cagttcagca actacagcgt cgatactgtg cgtatagaca     960
acgagacata cctgatagac tcgcagataa ccgtgagtcc tacagtgggc gtctcagctc    1020
cttatttcgc taactgagag tgattaacta caggtcgtta gactgatagc ggcctgactg    1080
atagtcacta acacataatt aactttgaga ggatataact atggaacgta atgctaacgc    1140
atactatgag ctgctggctg caaccgttga ggcatttatc gagcgtattc agtacgacca    1200
cctgactcaa gatgacgact acagcgctgc gctgcatgag tcgtagacg tcaggttcc      1260 acactattac cacgagattt ttacggtgat ggctgctgat ggtatagaca acgagttcga    1320
agactctggg atgatacctg aaaccaagga cgtaacgcgt atcctacaag ctcgcatcta    1380
tgaggcactt tataacgacg tgtctaatag cttggatgta gtctggtttg aggatgaaga    1440
```

```
ggcagacgaa gaggatgaat attgggtagt tgacgctaaa acaggcgcaa taattgtgca   1500
agctgtagct cttgaggtcg ctactgcatg tgccaaggtc aactatgtga taggtcgcca   1560
ccttcaggtg gaagacatca atgataacgt agtgtttgac cctgctgctg aggactgcga   1620
gtgatggtaa cttatggcct ctgccagcac cacgtcacta acgcccggct tatggtcaag   1680
accgggcagt tagaccacga ttgggctatg cgtctcttga aagtggtcta caggagacgc   1740
aagcgtatac acgacagttt acacgctaag tgacagacta caggtcatca atgctggtgg   1800
cctgactgat agtcattaac aactgagagg gaagatatga acacaatcac tggtgccata   1860
accaaaggtt ttcgagcaat tttcggtgaa acgcaagaag tatgcaccaa tcataaattc   1920
gtactttctt gcgtagcagg tgacgagttt gacgggttcg ataaactggt ggtttgcgac   1980
cattgcggac aagaggctat ccaacactca aacggtaaat ttgaattaat agacgatagc   2040
cttacagaag gagacggcga gtaacctaaa taaacaggag agaaccaaat catagcttga   2100
ccataacact gacgtgatgg tactgagtga tagacgagag gtcatcgact gataggtggc   2160
ctcaaagatt accacttaca ttgataggag ttaactatga gcactgcaat catctggact   2220
atctcaggct tcgtagcgtg gggaatgttt actctagtct gcaaactacc ggtccttact   2280
caactgttat ggggcttatg actatgagta tcgcactatt gatagccata ggctatggac   2340
ttatcgccta cgtgctggtg agagacatca acaaagcgcg taaagtctac aaattcaaat   2400
atgtacgtct gggtagctgg actgtacgtc aacctaacgg acgattcatg cgtaacttag   2460
cgaacgtctg gatatagcaa acacttggga gcaaactgta atgaacaagt catacgggat   2520
taatctggta cactctatgg acgcagacat gcaaatgtta agcctactgg ctaccgggta   2580
tcgtcacgga acgtcaagtc actccgcacg tcaacagcag gagcgggacc gggtactgca   2640
agcaagactc cgggctgagg gccataagtc cgaactaatg tgtctggtgt atggtggacg   2700
accaatcact gacgatggta aactttttagt ctcaggctgg aaggcgatag accaacggtc   2760
aaccatcaag cacacgactc atggtgactt cagtcatctc cacgctaacc cgctgatatg   2820
caagtaattc tgacttaact atcactatag gactcaaggt ctaagactcc aagtgaaaga   2880
ccaaagagac tttaagtgaa agactaataa caaggacttt aagtatgagc gtcatctcta   2940
ttgacaagca cgacttctct gatgtgtcga acgccattga gccgtttaac ctactggctg   3000
accactacgg gcaagacatt gcagtcaaac agcttcagct tgagcacgag gcatacactg   3060
aaggcgagcg acgtttcatc aagaaccttg agagacagac tgagcgaggg gaactggcag   3120
acaatcaggt cgccaagcct ttgatgcaga ctctggtccc taagattgcg caagccgtca   3180
aggagtggca tgaaggtcca gacgggaagc tgtcaacctc tcgtccgagc gtagcgttca   3240
ccatgttgag cactgaagag aaggccgtaa aggtccgctc tttgcgcatc tcctgcgagt   3300
ctgctgcggt tatcatattg aaggtcatac tctccaagct ggtcaagcct gaagggatac   3360
cgattacacc gatggcctca gcgataggtc gcacacttga ggacgaaatc cgcttcggtc   3420
gcatccgtga caaggagaaa gagcacttca agaaggcgat agctgataac ctgaataagc   3480
gggccggggc gtcctacaag aaagcctaca tgcaagcggt cgaggcatcc atgctggagc   3540
aaggccaact ggaagatgcg tgggggactt ggagtccgac cgaggctgtc cacgttggaa   3600
tcaagatgct ggagattgtc atccagtcca cacaactggt cgagcttaag cgttacggtg   3660
ctggcaatgc agcggctgac gttgagatgg tccacctgtc agacttctgg gtcaagaaga   3720
tggcacaacg aggattcagc cttgcgggta tagctccagt ctaccagcct tgcgtcgttc   3780
cacctaagcc gtggactggt gtcgtaggcg gtgggtactg ggccaaagga cgcagaccat   3840
```

| | | | | | |
|---|---|---|---|---|---|
| taccactgat | tcgcttaggg | tctaagtctg | cggtagcacg | ctacgaagac | gtgtatatgc | 3900 |
| ctgaagtcta | tgacgctgtg | aacatcattc | agaatacacc | ttggaaagtg | aacaagaagg | 3960 |
| ttctggaagt | ggtgaacatg | gtcgagaagc | tgaacaacac | gcctattgat | gacatccctc | 4020 |
| agatggaacc | gctgaagcct | gaggactatg | cgggtgagac | tgaagaagaa | ctcaaggcat | 4080 |
| ggaagaaggc | tgctgctggt | atctatcgcc | gcgagaaggc | cagacagtca | cgaagattgt | 4140 |
| cactgagctt | tatcgtcaac | caagcgaaca | agttctctca | gttcaaggcc | atctggttcc | 4200 |
| cgtataacat | ggactggcgc | ggtcgcgtct | acgctgtgcc | gatgttcaac | cctcagggta | 4260 |
| acgacatgca | aaagggtctt | ctgactctgg | cagtcggtaa | gcctattggt | gctgatggtt | 4320 |
| tcaaatggct | gaaggtccac | ggtgcaaact | gcgcgggtgt | cgataaagtc | accttcgagg | 4380 |
| agcgtatcaa | gtgggtggaa | gataaccacg | acaacatcat | ggctgctgcc | aaggcaccga | 4440 |
| tggatagcat | tgagtggtgg | ggcaagttag | actctccgtt | ctgcttccta | gcgttctgct | 4500 |
| tcgagtatgc | tggcgtaatg | caccacggct | tgtcttactc | ctgctcgctg | ccgatagcgt | 4560 |
| tcgatgggtc | ctgctctggg | attcagcact | tcagcgctat | gcttcgcgac | cacatcggtg | 4620 |
| gacatgcagt | aaacctgacg | ccatccggta | aggtccaaga | catctaccgc | atcgtgtctg | 4680 |
| accgcattga | ggaggagctt | aaagtcctac | tggttaacgg | tacggacaac | gagatggtaa | 4740 |
| ctcacgagga | caagaaaact | ggtgagatta | ccgagcgtct | caagctgggg | acacgagagc | 4800 |
| ttgcccgtca | gtggctgacc | tacggtatgt | cacgaaaggt | cactaagcgt | tcggtcatga | 4860 |
| ctctggccta | cgggtcgaaa | gagtacggct | gaggacatcg | tgatgccagg | acatcgtga | 4920 |
| tgccagcgat | tgactcaggg | tctggcgcta | tgttcactga | accaagccaa | gcatctcgct | 4980 |
| tcatggctaa | gatgatttgg | gaagctgtga | gtgtgaccgt | agttgctgcg | gttgacgcga | 5040 |
| tgaaatggct | tcagggtgct | gccaagctgc | ttgctgctga | agtgaaggac | aagaagactg | 5100 |
| gagaaatcct | gaagccttgt | cttccggtac | actgggtcac | acctgatggt | ttccctgtct | 5160 |
| ggcaggaata | ccgcaagaag | gacaccactc | gtctgaacct | gatgttctta | gggtcattca | 5220 |
| accttcagcc | taccgtcaac | aaaggcacga | agaaagagct | ggacaagcac | aagcaggagt | 5280 |
| caggcattag | cccgaacttc | gtccactcac | aagatggtag | ccacctccgc | aagactgtag | 5340 |
| tccacacgca | ccgcaaatat | ggcgtgatgt | cattcgcagt | gattcacgat | agcttcggga | 5400 |
| ccatcccggc | tgacgctgag | tatctgttcc | gtggagtccg | tgagacgatg | gtcgagacct | 5460 |
| accgcgacaa | cgatgtgctg | cttgacttct | acgagcagtt | tgaataccag | cttcacgaga | 5520 |
| gccagagaga | caagttgcct | gagcttccga | agaaaggtaa | actgaatatc | gaagacatct | 5580 |
| tgtcttcaga | ctttgcattc | gcttaacaac | aggagaagta | tatgtcaatg | aaacttgtag | 5640 |
| cacacaacag | ggtattcaac | gatgggtcgg | gacgttgcca | tgtagagctg | acttataagg | 5700 |
| atttaatcat | tctccgagac | agattacagt | cgggtgtgac | tgggtggatt | caacctaacg | 5760 |
| agtacaacct | tatagcttcg | attgatgaag | ttcttaacgc | gtggatggaa | gacgagcgca | 5820 |
| ttcagtatcc | gtcattccct | ctaattagat | aaggagagag | ttatgaaatt | tgcacacaag | 5880 |
| catactggcg | ttaatggtgg | gactcaaatc | gtgaccgtaa | cagaacacaa | cggcaagggt | 5940 |
| ctggtgaaga | ccacggtcat | ccctaccgag | atgtccaagc | agcttaacat | cccgttcaag | 6000 |
| actcttgtat | atctggtcga | gtccagccac | gagaagtacc | tgaaggacgc | agtgtccaag | 6060 |
| ctggagcagg | ccaaatgaca | gacatacagt | tactggcctt | gtggctggga | gcactcgcag | 6120 |
| tattcacttt | aatccaacgc | agaagaggtt | aaccctaaac | tatcactata | ggattagact | 6180 |

```
caaggtcatg actcaaagtc gtggccttca tgattaaccc taaataaaca ctactggaga    6240
tttaaccgta tgtatcagaa cactatcaac ttcgagcgca tccgtgaacg tcagcagact    6300
gaaggttaca tccctaaggg ccgcaagctg aacaagacta acgtggagg aggtatcaaa     6360
ggtgctttcc gtaacgctga aggtaaagac tctatggtta accaagaaa atacttcgta    6420
ggagcataac caaatgggca gactttatag tggcaacctc aacgatttca aagcagcgtg   6480
tcacaggctt tatcagttag acttcgctgt catatctcag gagtttcaag actatacgtc   6540
acgccaagag tgtatgaaac tcagggtgga ggaccgagct ggtaacatct tcgcgcttga   6600
gaccttcgca cactacgatg aagacgtgct gtataatacc gcaaccgact acctcaacgg   6660
tctcgctgac catctcgaca catggagcaa agaataatga caactatcaa aactaaccct   6720
caccgcgctg tagattactc tgagtctgga attaagaagg cactggaagc agccgggtct   6780
ctggaagctg aagtgaagta cgatggtgtg cgcctgaacc tcctggtcct gcgtgaaggt   6840
gagacctact ggcttagccg cgagtcgaaa cctctaccag ccttggagtg gatgaactct   6900
gagttaggta atgcgtggac ccaagctgac tggcgatggt tcctgcgtca atccggctac   6960
gaaggtgtgg gcatgatgat tgatggcgag gtcatggtca aaggtgtaga cttcaacacc   7020
tcctcaggtc tcatccgaac gaagtggctc aagcctaaca acgaggagtt cgctgaatac   7080
tattcgccgg cgactggtgg aaagaagctc ccgttctggg gatcccggtc acgacttcag   7140
gttgtggtct acggtgtcat cgacatgaca accattgctg acccgaaagc cgaaggtcct   7200
atccatagcg tcacacgcct gaaggccgaa gctatcgtcc ctctcctcca gaaatacttc   7260
ccggaaatcg actgggttct gtctgagtca cacacggtct atgaccttga gtctctcaac   7320
tccctgtacg aagagaagcg tctggaagga cacgagggtc tggtagtcaa ggacccactt   7380
ggtaaataca agcgcggcaa gaagtcaggc atgtggaaaa tgaagccgga ggacaccatt   7440
gatgggaccg tgtgtggact cgtgtggggg actcctggta aggctaacga aggtaagatc   7500
atcggctttg aggttctact ggaggatggc atggtggtca acgcctgcgg tctgtctgaa   7560
gaacagaagg acgggtttac ggctaaggtc aaggaggaca cgcttgctgc ggttggcatc   7620
tttgcgccgt acggcattgg tggtaacgaa ccttgcttcg ataacccata cgaaggctgg   7680
cagtgtgaag tcctcttcat ggagaggttc cctgatggct cccttcgtca ccccagcttc   7740
aagtgctggc gtggaaccga agacaaccca acgtgaagt catgagtaca aactttata    7800
tcaacatagc aagtagtcaa ctctacgctg tggtaaatgg cgagctgtgg tatcgtaaac   7860
tcaagaagtg ggccaagtcc tcctacgatg aagagacaat atcaaccatg agtcatcgct   7920
accgtaaggc tgctaaggtg aacaacttta agatgcgtta acgtcaaccc agtggtctta   7980
tgactgctgg gtttctttgc gtacgggcca ccagctagac cctaagctat cactatagga   8040
caaccctaac cgaccaaagg agaaaccta tgtctaaaaa cttaatgttc aaccgattta    8100
ctcgaagctt ccacctgtcg catagcccat tcagcttcca taaatctaat caaccattac   8160
cccgctttgg taagacagtg gctctgtctc ccacagttca tgcgctagtc acccgcaagt   8220
ctatgctgaa ggctatggat aaagaacaag tcgatgtacc tgtggtcgtt acaaaatggc   8280
ctcgcattaa gctggccctt ctggtaatta aggaagtgtt ttgatggcat attgtgatag   8340
caccacatac tgtgaagcat gtaatggtga tgaccgcttc ccacacgttg gtaaacttgt   8400
aggtaacaag ctgcaagaaa ttgatggtgt acgcaagcca tcccactatc aggtctttga   8460
tggcgtggaa tccattgaga ttatcgcacg gtcaatgact gtgagtgagt tccgtgggtt   8520
ctgcatgggt aacgtcctga agtatcgact ccgggctggt aagaagtcag agctggcaac   8580
```

```
tatggagaag gacctgaaca aagcagcctt ctatcaggag ctgttcgacc tgcataaagg    8640
taagtgctat gcttccgagt gagtggtgtg aaatgatgtt cgagaagaca ggtaacactg    8700
actaccttga attgtataac cagtggaagg agcgcggttt atgactgagg ttgagaagaa    8760
atacatcgtg gagcttgagg gtcgcgttca gtccttcgag gttccgttgt acgcaaagtc    8820
tcttgaagag gctaccctga agtcccaaga gtatgaggac gctgggtttg tggtcggacg    8880
gattcgccct gagacctaaa ctatcactgt aggacagacg tccagttagt aactttaaat    8940
taggagattt acaccaatgg ctaaagagca actgaagact ttcaccactc cggtagctgg    9000
tatcgttgag ccttacgcat ggctgaacaa agcagacacc aagtttaatg aacgtggtga    9060
gcataaggtt aacctgacgt tcgacctgag cgacccgaag gtccgtaaga tgattgatgt    9120
cttacagaag attcacgacg atgcgtatgc gaaagcactc gcagaccacg agaagaaccc    9180
acctcaggtt cagcgtggca agaagcctat tgaaccacgt gaaggcgaca tgccgtggat    9240
tgagaatggt gacggtactg ttacccttaa gtttaaatgc tttgcgtctt acctgaaaga    9300
cggcaagtcc gagcctatct tattacggtt ctacgacacc gatgctaaac tcatccgtga    9360
cgtcccgaat attagcgctg gctccaaact gaaggtcaag tttaaagtcc tgccgttcaa    9420
gtggaacgct gcgaccggtg caagcgttaa gctccagctt gagtcctgcc ttcttgtaga    9480
actgaaggag tggaaaggtg ctggtggtga tggtggctgg ggtgatgatg aagaccttgg    9540
tactggctac aaagcgccaa ccgatggtga cttcgggtct gatgccttcg gtgacgatgg    9600
ttccgaaggt ggtgacgact ccagctctgg tggcgattac gacttctaat ggcccaatgg    9660
tctgcaaaac gggggcactc tgtgggtgcc taccgctctg gacttgaagc caagaaccag    9720
cagtggctgg aacagaacgg cgtcaaagcg gagtacgaaa gccattatat caactatgtg    9780
attccggctt ccgaccacaa gtacacacca gattttatcc ttcctaacgg tatcatcgtg    9840
gagaccaaag gtatcttcga tagtgatgac cgtaagaagc accttctggt acgagaacag    9900
cacccagagt tagacatccg gttcgtgttc tcaagttcac gctccaagtt atacaaaggg    9960
tctccaacca cgtatggcgc atggtgcgaa aagaacggct ataagtatgc cgataaattc   10020
atcccggttg agtggcttcg agaggcgact gtacgtctgc cttcaggtat actcatcccc   10080
aagaagaaag gagttaagtg atgagcaaga agtttaaact gttagtagat gcgcatggct   10140
ggcctagtgg gactatagtt accaagtgtg agaatgaccc cgtaccagat tcaagaatga   10200
ccctagttga gtgccagatt ccaggcgcat acaaacatgg gtctaacggc tgcaatactc   10260
agcctgaggg tatgtgggga gcatgggtcc ttaattggaa acttgaggaa atcaagccgg   10320
aagagaaact cactggtgtc caaaccactc aagtcctgcc agcttcgagc gtaccgcctg   10380
tgactttgaa gcgtgaagtc ctgaccatcg acaagattgg tgtaggccag acgttcatcg   10440
tccatggaaa gcctgaagaa gtttacgtga agattagcaa ctcacacgtc ttcaaccata   10500
agcatctcca gatgcacacc acggacgcac aacgcttcac ccagcacctg aatctggttg   10560
tcgtagaatt ggtggtgtac aatggtaagt aaggtacagt tcaatccacg gtcccggacc   10620
gacgctatct tcgtacactg ttcggctacc aagccagaga tggacatcgg ggtagagacc   10680
atccgtatgt ggcacaagca gcaaggctgg ctggacgtag ctaccacttt atcatcaag    10740 cgcgatggca ctgtggaaga gggacgcccg gtcaatgtcg tagggtcaca cgttaaggac   10800
tggaactcac ggtctgtagg cgtctgcctt gtaggtggaa ttgacgctaa gggcaagttt   10860
gaagctaact tcactccggc ccagatgaac tccctgcgca caagctggc tgacctgaag   10920
```

```
gacttgtatc ctcaggcaga aatcaaagca catcatgacg tagcaccaaa ggcgtgtcca   10980
agtttcgact tgcaacgctg gctgtctacc aatgaactgg tcacttccga ccgaggctaa   11040
actatcaccg tagggatgag accacgagtc ttgtcccttt gttcgcattt gagattaaga   11100
aatgtctcca tagctcaaac ggtagagcgg cgggtcgtga tggcctattg cgattagggt   11160
tcgaatcccc gtggagacgc cactaaggag tgaccaatgt catacgatga ccaagacgac   11220
gagagtgtct ttctgtatca cacccagtgt ccagactgtg ggtcctcgga tgccaatggt   11280
gtttactcag atgggcacat gtactgcttc gcctgtgacc cttcagtcgc atggaagaaa   11340
ggagacatgg agttgaccga ggggtacaca ccctcaggag gtagaaagca agtgagcaat   11400
ctgttaacgt tcggtgagaa cgctggacga tatgtcccac taccagcccg tagtctcagc   11460
atggagatat gcaagaagta cagctactgg gtgggtaaca tgggcggcaa gatggttcag   11520
gtcgctgatt attacgacag gtccgggacc aaggtagggc agaaagtccg agacgctgag   11580
aagaacttca cggctatagg tagcgtcaag tctgacatgc tgttcggctc tcagctctgg   11640
aacggtggta agaagatagt catcaccgag ggtgagatag acgctctgtc tgtggctcag   11700
gtgcaggacg gtaagtatcc agtggtatca cttccgttag gctccaagtc tgcgaagaaa   11760
gctatggctg cgaacattga gtatctcgac cagttcgaag agattatcct gatgttcgac   11820
atggacgaac cgggtcgtca ggccattgag gatgcagctc cagtcttacc agcaggtagg   11880
gtcaaggtag cgttcatcaa tgggtacaaa gacgccaacg ctgcgcttca ggccaaggac   11940
ttcaaggcca tcaccgatgc tatctggaac gctaaacctt tcgtcccggc tggagtggta   12000
tcagcggcaa gcctgaagga ccgcacacga gaggcaatgc ttaaagcaga gactgaaggt   12060
ctcatgttct cgtcatgcac aacactcaac gcgatgaccc tcggtgcgcg agctggtgag   12120
cttatcatgg ttacttcagg gtcaggcatg ggtaagtcca ccttcgtccg tcagctactc   12180
ttagagtggg gcagaggtgg taagcgtgtg ggcatggcta tgcttgaaga ggctgtagag   12240
gaaacagttc aggaccttat gggtctggac aataacgtcc gtctacgcca gagcaaggaa   12300
ctgaagcaag ccatcttaga ggacggacgg ttcgacgaat ggtatgacaa gctgttcgga   12360
gacgataagt tccacctgta cgattcattc gcagagtcag aggaagacac cttgttcgct   12420
aagttatcct acatggtgga tggtcttgac tgtgacgtca tattgctgga ccacatctca   12480
atcgttgtgt cggcatgga agataactca gatgaacgca agaccattga ccgaatcatg   12540
actcgtctca agaagtttgc gaagacgaag ggcgtggttg tcgttgtcat atgtcacctg   12600
aagaacccag aaaaaggtaa atcgcatgaa gaaggacgac ctgtttcaat cactgaccta   12660
cgtggttctg gtgctctacg ccaattatct gatactatca tcgcacttga gcgtaaccag   12720
caaggtgata ctcctaacgt tgttcagctt cgtctactca agtgtcgctt tacaggtgat   12780
acgggagtgg ctggacacct cgagtacaac aagacgaccg ggtggcttga accgattagc   12840
ttcactggca gcagcggaga agaggatagc ggctcgtggg aaaacaacga cttctagtcg   12900
ggacatcgct gactataaga attttacgga ggaccgttag tgttaaagaa acttaaagct   12960
cgctaccatc ggttcatgta caaatggtgg agcgacgaag caacctgcct gtcgaacatt   13020
ctgggagacc agcggttcaa ctctgaggca tggaagaaag ctaaccggaa gttcatgtat   13080
cacttcttgc gtacagactt ctaggtctag actcaaggtc attcacatag agtggccttt   13140
atgattagac taaacggagg attaaccatg tttgacctta agagtatctg gggttctgac   13200
atcgagacca acgtctcct tgatacagtc tcccagtttc actgtggggt cctgattaac   13260
gccgagtcga atgagaccct taagtatggg gtagctccga tggtcggtat cgtcggtggc   13320
```

```
ttcaaagagt atgtgcagaa ggtggaagag attgccgcat cacctgatgg tatgctggta   13380
ttccacaacg gtatcaacta tgacgtcccg gctattgaca agctgaagcg tctgtacttc   13440
gggaaacgct ttaacttccc gaaacacaag atgattgata ccttggtgct gggtcgcttg   13500
atgtatccca acattaagtt ctcagacatg ggcgcagtga agctggtcg tctgccacct    13560
aagatgatgg gacgccagtc tcttgaggct tggggctatc gtctcggtga tgaaaggt     13620
gagtacaaac acgattacgt tgccaagtgc aaggctgaag gtatcgaata taaggctggg   13680
gacgaatggt tgttcccgtc tcaggagatg ctagactata acgttcaaga cgttgtggtc   13740
acactggcgt tgttcaagaa gttcctgact gacaagtatt acttccagtc tgaacagttc   13800
gctttcgacc agatttatgc gttgcgtctg aacatgatg ctgcgtggac ctgtgcgaag    13860
atggaacgta acggctatcc gatgaacacc gagatggtcg aaggcttata tcgtgaactc   13920
accgtcaaac gtgcagagct gctggacaag ctgcgttcga ctttcggtag ctggtacgca   13980
ccaaagggcg aaaggagtt cttcaagcac ccacggacag gcaaggacct tccgaagtat    14040
ccgagagtcg tgtatcctaa ggtcggtggc atctttaaga agccgaagaa caaagctcaa   14100
cgcttaggtc ttgaaccctg tgaacgcgat acgcgagaca cgatggaggg agcaccattc   14160
acgccaatca cttacgttga gtttaatccg ggaagcggag accacttagc gaaagtcttg   14220
atggagcgtg gctgggagcc tgtggacttc actgacaccg ggaaacctgt agtcgatgac   14280
gagacgttgg aacacgttaa gttaccagac gcagaggctc aggcttgcgt agagctggtc   14340
cgtgagtatc tggtagtcca gaagcgcatc ggtcaggcgg ctgaaggtaa gaacgcatgg   14400
ttgaaacttg taggtcaaga cggacgtatg cacggttcaa tcaacccatg cggggcagta   14460
accggacgtg cgacccatag tgcaccaaac atggctcagg tacctgctaa cggtgctccg   14520
tatggtgaga cttgccgtgg tgctttcggt gcagcgtgga caagaagga cggcaagcca   14580
gacccttggg ttcaagtagg cgtggatgct tcaggtcttg agcttcgttg tctggggaac   14640
cgagcggcac cgtttgatgg tggcgactat gctaagactg tggtagaagg cgacatccac   14700
tgggccaacg cagtcaacgc tgggttagca cctaacgtcc cacgcgacaa gtcgagccat   14760
gaccacgatg ctttccgtaa taacgccaag acgttcatct atgcgttcct gtatggcgca   14820
ggggccgcta agattggact gatagttggt ggtggtaaga aggaaggtgc ggccctgatg   14880
aagaaattca ttgagggtac accagctatc aaggacctca gggaagctgt gagtaatacg   14940
ttaatctcag actctaagtg ggtggacgga gagaacatcg ttaagtggaa cgccgttgg    15000
ctgcgtggac ttgatggtcg ccgtatccac atccggtctc cacactcagc actgaacgca   15060
ttacttcaag gtgatggtgc ggtagtctgt aagacttggt tcacttggct ggagcgtaac   15120
ctcgaagcta agggctatgt tcacgggtgg gatgggggact ttgcgattat ggcatttgtc  15180
cacgatgaag ttcaggttgc tgcccgcacc atggagattg ctgaggacat cgttaaggtt   15240
gctcagtcca cgatgcgcga ggtgggtgag ttctatcagt ttaaatgcgt attggacacc   15300
gagggcaaga taggccctac gtggaaagaa tgccactaag gaggtgcaga tgggcggtgt   15360
agccactctc cgcttccaca agatgcctac gggttgtatc gtttgtgtat cccaccgtag   15420
aaatcaggat gggtactttc ggtatactgt aggctctgcc cgtaagccgg gacgtaaagc   15480
gtttatgttt caccgctggg tctgggagca acaggtcgga ccgattcctg agggattcga   15540
gatagaccat ttgtgtttaa accgtgggtg ctgtaacatt gagcacttgc agtgtattga   15600
cgggaccgag catactgtca agaccaaccg tgagcggaag ctcatcaaga agaaataagg   15660
```

```
agaaagctaa tggctatgac caaacgcgct atcgtaagtt tcaaccttaa ggctgtactt    15720
cctacagacc aagaggaaat catcattggt ggtctgcgtg agctggctaa gagcgttaac    15780
tcaggtgaaa tcgagcctga cggtaagcag cgccatatgt tgaccctgtg gctaacagaa    15840
ggtatggact cggtgattga gttcgttctg cgcgctagct tacggtcaat ggttaaagat    15900
gctgtacagg aatattcaga ctcagagttc ttcagtgtct caccagccac cgtgaggttc    15960
aaacaatgag tgaatactta cgggtcctag cggccctcaa gtcctgcccg aagaccttcc    16020
agtccaacta tgtgcgcaac aacgctgcac ttgtggctga ggctgcgagt cgtggacatc    16080
taagctgcct gtctatggat gggcgtaaca acggtgcgtg ggagattacc gctgctggca    16140
ccaagttcct gaaccaacac ggaggatgcc tgtgagcgaa agaaaatag ctctggtgct    16200
agacggtgac tacttagtgt tctcttctat ggctgctgcc gaggacgaga cagactgggg    16260
tgatggcatc tggaccctta tctgcgacca tgagaaggct cgtcgtatcc ttgagaacac    16320
catcgctgaa atcgttaaga agcgtaaggc gtggaaagac gctaagattg tgatgtgctt    16380
tactgacgat aacaactggc gtaaggacgt gctacctacc tataaggcca accgtaaagg    16440
ttctcgcaag cctgtaggtt acaagaagtt cgtagccgaa gtgatggctg acccacggtt    16500
caacagcttc ctacgtccta cacttgaggg tgatgactgt atgggtatca tcgggacacg    16560
acctcagatt gtaggctgtg accatgctgt tctggtgtcc tgcgataagg acttcaagac    16620
catcccgaac tgtgagttct tctggttaac cactggtgaa attctaagtc atactactgc    16680
tgaggcagac tactggcaca tggagcagac catcaagggt gacactacag atggctacgg    16740
tggcattccg gggatgggcg aggatactac tcgtgcgttc cttgacgagc cgtactactt    16800
cgtgcaggag agccgtgagc ttaagactgg caagaacaaa ggccagatta agactgagtg    16860
gaagaagtat cctaagcgtg aagacatgac gctgtgggac tgcatggtga ctctggctgc    16920
taaagctggg atgaccgagg aggaacttct ggtccaagct caggtagctc gtatttgtcg    16980
agcctccgac tacgacccta cgtccaagga ggtcatccta tggacaccat ccatgtaatt    17040
tactgggtcg gacttctggc cctttactgc atgtacaagt ggttcgggtc gaacaaccgt    17100
cctaaacact gagtctaacc gatagtcata tcctatcaat ccaatagtca tccataggtg    17160
aaacactaaa ctatcactat agggacttta ggacctaaga tatgactata agatagactt    17220
tagtcttaac ttaaagagga gattcaagat ggcgattaat gctattgaaa acgttgttaa    17280
gcagttacag gaagaaagac ttgatgtccc gaacatctcc cagtctgcca tccagttcat    17340
gcacgtactg ttcaacgcaa gctacgctga aagactggga gctatcagtc tcctcaagca    17400
gcaaggctac agcgatgcgt tcattgccgg attcatcaag ggtctccagt attgttctga    17460
cactctcgac tctgcgattg ctatgcgtcg tgagctgaaa gataccgttc agttcgatta    17520
actgtaggag ggactatgtg tttcagtcca aagattagca ctccgaagcc ttcggtccaa    17580
gcgcctgaac cagcacctct gagtgaggag gttgcgtcag ttgacatcgg ggctgaatcg    17640
gatgtggaca ccaacgagac caaaggtatc aaagaccttta aggttaagaa ggagtctgca    17700
cctaaagata atcgtcagt gagtcgcgct atgcgagcct ctggcgtaaa catggggtaa    17760
gacaatgcta ccatatctca actcacgcga aggtcgccac atgtgcgcct gccgcctctg    17820
ggaagacggg cagtctaact tcaagtcatt cgaggacttc aaggctcata cttaccgtat    17880
tgctgacgag ttcgacggtg aagagtacac aatctacgat gtctcaggtc aaccagtagc    17940
gtatctctac atgctggcta ccacatcttg gcaccgaccg actcccggtc ttgacctttc    18000
aatcgtcgct attcgtcgtg actcgcagtc ctcccgcaag gttcttgaga ctgtcaggta    18060
```

```
catcatagac gaagagtgca agcgttgggg tcttggctgg tattctcgtg tcaagcatgt    18120
ttccgggtcg gtagacatcg taacaaccaa gtgcgttagc gcgaacaagg agattaaccg    18180
tgggtaaatc aatcagtaag gccttcagta aagtagtaaa aggtgcttta gggaccgttg    18240
gtcttggttc taacgatgca cctaaggttg ttgaggctca gacccagca gcaccagtgg    18300
aagtaccgaa cgacaaagtg gaggatgtgg atactgaaac aaccgcatct gacgagaaga    18360
aagtgaagcg ctccggtaag cgtagccttc aggtctctcg tacatctggt ggcggtattt    18420
ctatataagg aggtgacgaa tggctgaacg tgaagggttc gctgctgaag cgctaagtc     18480
agtttatgat agattgaaga acggacgaca gccttacgag acccgcgcac agaactgtgc    18540
tgctgtcact atcccgtcac tgtttcctaa ggaatcagac aactcgtcta ctgaatatac    18600
cactccgtgg caagctgtag gtgctcgctg cttgaacaac ttggctgcaa agctgatgtt    18660
ggcgttattc cctcagtcac cgtggatgcg actgacagtc tccgaatatg aggccaagac    18720
cttgagtcag gactcagagg ctgctgctcg tgttgacgaa gggcttgcta tggtcgagcg    18780
tgtgttgatg gcctacatgg agactaacag tttccgtgtg ccattgttcg aagctctgaa    18840
gcagcttatc gtctccggta actgtctgct ttacattcca gagcctgaac agggtactta    18900
cagtccgatg cggatgtacc gcttagtgtc ttacgttgtt caacgtgatg cgttcggtaa    18960
catcttgcag attgtgactc tcgacaaggt agctttcagt gctctaccgg aagacgtgaa    19020
gtctcaactc aatgcagacg actatgagcc tgacaccgag cttgaagtgt atacgcacat    19080
ctaccgtcaa gacgacgagt atctacgcta cgaggaagtg gaagggattg aggtagcagg    19140
gaccgatggt tcctacccgc tgactgcatg tccgtacatc ccggtacgaa tggttcgact    19200
ggatggtgaa gactacggtc gttcttactg cgaggagtat ctgggcgacc ttaactcgct    19260
ggagacgatt acagaagcta tcaccaaaat ggctaaggta gcctccaagg tggtgggact    19320
cgttaacccg aacggtatca cgcaacctcg acgtctgaac aaggcggcta caggtgagtt    19380
cgtggctggt cgcgttgagg acatcaactt cctgcaactg acgaaaggtc aggactttac    19440
gattgccaag tcggtggctg acgctataga gcaacgttta ggctgggcct tccttcttaa    19500
tagtgctgtt cagcgtaatg ccgagcgggt cactgctgaa gagattcgtt atgttgctgg    19560
cgaactggag gcgaccttag gtggcgtgta ctcagtacaa tcacaagagc ttcagttgcc    19620
tatcgtccgt gtgctgatga accagcttca gtctgctggc atgattcctg accttccgaa    19680
agaagcggta gagcctacgg tctccactgg tcttgaagcg ttaggccgtg gtcaagactt    19740
agagaagcta actcaggcag tcaacatgat gaccgggcta cagcctctgg ctcaggaccc    19800
agacattaac ttgccgaccc tgaagctgcg actgctgaat gccttaggca ttgacaccgc    19860
tggtctactc cttacgcagg acgagaagat tcagcgcatg gctgaacagt cgtctcaaca    19920
ggcagtagtc caaggtgctg gtgctgctgg tgccaacatg ggcgctgctg taggtcaggg    19980
agctggtgag gacatggctc aagcctaaac tatcactata ggaacaacac cgtaagtcca    20040
actctaggtg agtcaactag acgaggcagg tgttacctat taactaccaa aggagagact    20100
taatgtccca atcagtttat gccgagttcg gcgttagtcc taatgcaatc actggttccg    20160
ttgaggacct gaacgaacac cagaagtcta tgcttgaaca ggacgtagct gttcgtgatg    20220
gcgatgacgc tattaccttc aagcaactgg aagccgaaaa cgaagaggct accgaagaag    20280
acgaaacgt cgaagagact gaaggtgaag aagaccacga gtcagatgat gaagagtctg    20340
agaccgatgg tgagcagccg gagttcatcg aactaggtga tgcgccgaaa gagctgactg    20400
```

```
aaagtgtcac cgctctggat gaaaacgaag ctgcattcga cgacatggtg tcttctgctg   20460
tagaagctgg caaggtcact gctgatgaaa ttaccgctat caaggctgaa tacgccaagg   20520
acggtaagct gtctgacgca tcctacgcta agttgcagga agcaggttac acaaagcgtt   20580
tcgtagattc gtttgtccgt ggtcaggaag ctctggctga acagtatgct gctggtgtgg   20640
ttcgctacgc tggtggtgct gaacagttta atcgcatcct gtcacacctt gagtccaacg   20700
acccgtcaac tcgtgaagca ttggaagctg ccatcgttcg taaggacatt gcgactacca   20760
aagctctgct gaatctggct ggcaagactc tgggtaaagc tgtaggcgtt aaacctcagc   20820
gtaccatcac caatcaggct aaacctgtgg ttgcacctaa ggctcctcag accgaagcat   20880
tcagctccaa ggctgacatg attaaggcta tgagtgaccc gcgatacctg cgtgacgcta   20940
agtacacgat ggaagttcga gctaaggtag ctgcctcaag cctgtaggac taaactatca   21000
ctatagggag accaagagac agactcaagg tttcccctat tacttaagtc catacggatt   21060
gggcgtacag taagtaataa actttatttt tcaattgaat aggagaatta tcatatggca   21120
aacgttccgg gtcagaaagt tggtacagac caaggtaaag gcaactctgg ttccgacgct   21180
ctggcgttgt tcctgaaggt atttgctggc gaagtcctga ccgcattcac tcgccgctct   21240
gtaactgcta caagcatat tgtccgtacc attcagaacg gtaagtctgc tcagttcccg   21300
gtcatgggtc gcacctctgg tgtgtatctg gctccgggtg agagactgtc cgataagcgt   21360
aaaggtatca acataccga gaaagtgatt accattgatg gtctgctgac tgccgatgtg   21420
atgattttcg acattgaaga cgcgatgaac cactatgacg tggctggtga gtattccaac   21480
cagttgggtg aagctctggc tatcgctgcc gatggtgcgg tactggctga gatggctatt   21540
ctgtgtaacc taccggctgc atctgatgaa aacatcgctg gtcttggcaa agcgtctgtg   21600
ctggaagttg gtactaaagc agacctgaac actccggcta agctgggtga agcaatcatc   21660
ggtcaactga ccattgctcg tgcgaagctg acatccaact acgttcctgc tggcgaccgt   21720
tacttctaca ccacgccgga caactactct gcaatcctcg cggctctgat gccgaacgct   21780
gctaactatg ctgcgctgat tgacccagag actggtaaca tccgtaacgt aatgggcttc   21840
gtggttgttg aagttccaca cttgactcag ggtggtgctg gggaaactcg tggtgccgat   21900
ggtatcacta ttgcgactgg tcagaagcac gccttcccag ctactgctac tggtgatgtt   21960
aaagttgctc tggacaacgt tgtgggcctg ttctctcacc gttctgctgt aggtactgtt   22020
aagctgcgtg acttggcgct ggaacgtgac cgtgacgtcg atgctcaggg cgacctgatt   22080
gttggtaagt acgctatggg tcacggtggt ctgcgtccag aagcagcagg cgcactggtt   22140
ttcacagcgg cgtcagcggg ttaacgacct ttaaggccct ctctacagag ggtcctacct   22200
tagagacgta tagttctacg gtgggaacca gcctgaaggt tgacttccct gagctttcag   22260
atgtgaccga ttggtcgctg cttgaggtga ctacgcctga tggtgttagc tactcccgta   22320
gaaccaacag tctctacttc aaggccacct ctggcgtgga aggtctggtg attgttgggt   22380
atgacgggac gcctgtgcgt tccttcaacg tatctttcac aaactaattg aaaccccttg   22440
ggtgccttcg ggtgcttgag gggtttttt gcttaaggag ggactatggt ccttatttac   22500
acagggttag cactattcgt cttattctgg gcgtacctgc tgtccagctc accgtctagc   22560
gcctatgacc gttaaggagt aaacctatgg ctcaatacat tccactgaat gctaacgatg   22620
acttagatgc catcaacgat atgttagcag ctatcggtga accagcagtc ctacagcttg   22680
acgaaggtaa cgctgacgtc tcgaacgctc aacgtatcct gcatcgtgtc aatcgtcagg   22740
tccaagctaa aggctggaac tttaacatca acgaagctgc tgtcctgacg cctgatgtcc   22800
```

```
aagacaacag gattagattc ctgccgtctt accttcgggt catgactgct ggtgctacca   22860
gttactacag caacatgggg ggctatctct atgacctgtc cactcagtcc acgaccttca   22920
ctggaccaat tacagtcgaa ctggtggaga tgaaaccgtt cgctgagatg cctgtagtat   22980
tccgtgacta catcgttacc aaggctagcc gtgagttcaa cgctaagttc ttcggtagcc   23040
cagagtctga actgtacctt cgtgagcagg aagcagaact ctatcagcag gttatggaat   23100
acgagatgga cactggtcgc tacaacatga tgtctgacat tgggagggac taatggctag   23160
tcacaacctg aagattcacc gccagcactt tggtccggta cagctaggtc taaagacagc   23220
agagctgaga cttaacgacc gggactttaa ggttggcgac tggcttatcc tgaatgagtg   23280
ggacaacggg tatactggac aacaggtagc acgtaaggtt gtccacattg ctgacgttgg   23340
tgacatcgct gagggatacg tcctaatgag tatgatttaa ggagggcata tgccgcttat   23400
tacgcaaagc ataaaaaatc ttaagggtgg cattagccaa cagcctgaca tcctgaggtt   23460
ctcagaccaa ggcgaggctc aagttaactg ctggtcatcc gagagtgatg gcctccagaa   23520
gcgtccacct acagtcttca agcgacgtct taacatcgac gttgggagca accctaagtt   23580
ccacctgatt aaccgtgatg agcaggagca gtattacatc gtgttcaacg ggtccaacat   23640
tcaggtagtc gacttgagcg gtaatcaata ctcagtttca ggtgcggtag actacgttaa   23700
gtcgtccaac ccgcgagatg acatccgtgt cgttacagtt gcagactata cgttcatcgt   23760
gaaccgtaag gttgtcgtta acggtggaag cgagaagtca cactctggtt ataatcgtaa   23820
agctcgtgct ttaattaacc tgcgtggtgg acagtatggt cgcaccctta aggtaggaat   23880
caacggaggc gttaaggttt cgcataagtt gccagcaggt aatgatgccg agaatgaccc   23940
tcctaaggtt gatgctcagg ctatcggtgc agctctgaga gaccttcttg ttgctgctta   24000
ccctaccttc acgttcgacc ttgggtctgg attcctgtta atcactgccc cttcagggac   24060
tgacattaac tcagtggaga cggaggatgg ctacgctaac cagctaatca gcccagtact   24120
cgacacggtg caaacaatct ctaagctgcc tcttgcagct ccaaatgggt acatcattaa   24180
gattcaaggt gagaccaaca gtagcgccga tgagtattac gtgatgtatg actccaacac   24240
taagacgtgg aaggagacag tagagccggg agtggtcact gggttcgata acaccacaat   24300
gccacatgct ctggttagac aatctgacgg ctcctttgag ttcaagactc tggactggtc   24360
taagcggggt gctggtaatg atgacacaaa ccctatgcct agcttcgtgg atgctacgat   24420
taacgatgtg ttcttctaca ggaacaggct agggttcttg tcaggagaga acgtaatcat   24480
gagccgttca gccagctact ttgcgttctt ccctaagagt gtggcgacat tgagtgatga   24540
tgaccctatt gacgtagctg taagtcaccc tagaatctca atacttaagt atgccgttcc   24600
gtttagcgag cagctactac tttggtcaga tgaggtgcag ttcgtgatga caagctcggg   24660
ggtccttacc tcgaagtcta tccagcttga tgtaggctca gagtttgcct taggagataa   24720
cgccagaccg ttcgctgtag acgctcagt cttcttctca gcgcctcgtg gatcattcac   24780
cagtattaag cgatacttcg ctgtagcaga tgtgtctgac gtgaaggatg ccgatgatac   24840
cactggtcac gtactgtcct atatccctaa cggggtgttt gacattcaag gtacagggac   24900
tgagaactac atctgcgtca actccacagg tgcatacaac cgaatctaca tctacaagtt   24960
cttgtttaag gacggcgtac aacttcaagc ctcttggtcg cactgggagt tccctaaagc   25020
tgataagatt ctggcgtctg cgtcgattgg ctctaccatg ttcattgttc gtcagcacca   25080
atggggtgtg gacattgagc accttaagtt catcaaggag gcaaccgact ttccattaga   25140
```

```
gccgtataga ctccacgttg actctaaggt gtctatggta atcccaattg gctcatataa   25200
cgctgacacc tatgagacta cggtcgacat tggttctgct tatggtggaa acgctccgtc   25260
tcccggtcgg tactatctga ttgacagtca gggtgcctat gtggaccttg gtgaactgac   25320
caacatctca actgtggcta tactcaatgg cgattggtcg ggacgtacag tgttcatcgg   25380
acggtcttat ctgatgtcct acaagttctc acggttcctg attaagattg aagacgatag   25440
tggcactcag tctgaagaca ctggacgtct acagcttcgt agggcttggg tcaactacaa   25500
ggacactggc gctcttagac tcattgtcag aaacggtgag cgggagttcg tgaacacctt   25560
taatgggtac acccttggtc agcaacccat cgggactacc aacattgggg acggtcagta   25620
tcgcttcgct atgaatggta acgcattaac cacgagtcta accttagagt cagactatcc   25680
taccccagtg tccatcgttg ggtgtggctg ggaggcgtca tacgctaaga aagctcgttc   25740
cgtctaactt attgaagggc ctatagattt accttaacta tcactatagg gactataggc   25800
ccttaaggtt ataaggagac tttatgtata ttcgcaaggc tacggaacag gatgtccact   25860
actttctgtg gcatctttca gcagatgatg ttaatgagtg caaagcaaac tacgggtcaa   25920
ccgtgggtct ctcagagaga ctgcttaagc atctatctcc gtcatctgtg gtttttaacga   25980 acggtgtagg tgaagtgttt gcctatggtg gaaaccaagg ggataacgta tggttcttga   26040
cttcgggtct ggtccacaag ctgagaccta agagaagcg agagttcata agcgtatct    26100 ctgagtacag ggacttaatg ttagaccaat acgggaccat ctggaactac gtgtggtcag   26160
gcaataagtc tcacattaaa ttcttgaagt tgcttggggc taagttccat gatgattgga   26220
ctatcagccc ggtaactggt gagcattttc aattattcac tatctctaag gaggacgtat   26280
gtgtgaaccc gtaagtatcg gcatgggtat catggctgta gccggggcca ctatgtccgc   26340
atcccagcag gcaaaggccg aaggtgcagc aattgacgct cagaaccgac aggctcagga   26400
aatggttaag cagatgaact actctgacgc caacctgaga atgcaggagc gagacctgaa   26460
ggagcagcag atggctgaat tgacagagac cacgctcaac ggtatacgca atcagggcat   26520
ggtcagagct gcagtggctg agtcaggtct ggaaggtaac tctatggaca ggattgaacg   26580
tcaggtcaaa ggagatacag tcaaggagcg agcaggatt accgaaagtt acaaccgaga    26640
ctatgcggct atcttcggga accgtatcgc caacattgag aacacaaagt ctgctatccg   26700
tggtcaaggt aaaatcatca agaccagccc actgggccat gcacttaatg ttgctagcgc   26760
cgggatgcaa ggttacgccg ctggtaagtc aatctctgga gcgtccagct ctggcggtgc   26820
tgcacctatt agtgctgcta aaggcacacc tacaggtcat agctaagagg aggaataatg   26880
gctagtaata ttgaatcagc tctggctaat cggactatgg gtcgtggcag ggctccgggt   26940
aaaactatcg ccgtcaacta tcaagcagcc agcgttcagg ctcctactgg tgactccggt   27000
ctggctcgtg cgttaaccaa cttcgttgag tctgggacag gattgtacaa gcagttcaag   27060
gacgaggaga agacacgggc cgacgagcgg tctaacgaga ttatccgtaa actgacacct   27120
cagcaaagac gtgaggctat ccagaacggt acattgctgt atcaggatga cccttacgct   27180
atggaagcac ttcgagtcaa gacgggccgt aacgctgcct tgcggttga tgacgagatt    27240 aacgttaaga ttcagaacgg tgagttccgt acacgtcagg acatggaaga gtatcgccac   27300
cagagacttc aggacgccgc taagtcctat gctgaagagg ctggtattaa ccctaccgac   27360
gagttcttcc agcgcgggtt caacgataac atcacagacc gaaacatcgc tatctatggg   27420
tctttcaata gtatttcag caagcagtct gaagagacag caatgttgaa cactcgtatt   27480
gagatgaact cgttccttaa cgatggggac ctgatgcgtt cgcctgagtc tggaaagacc   27540
```

```
ttcatggcct accttcggga tggactgacg actgctgcta tcccttcgga ccagcgagca   27600
cgagaggtaa tcacccagac tgtccgtgac gcaatccaga agtcaggagg ctcaaacttc   27660
ctacagcaag tccgtggcga gcgtatcacc cttaacggtg tggacgctac agtcgaagag   27720
attgtaggcc ctgacgtctt caatgctgct gtggttgagg ctcaaggtac cgagtacaag   27780
ttggtggcta agtatcagga agacttatcg ttaggcgttc agtctgcgat tcttcaggac   27840
gacccaacca tcggtctgga ccagattcag aaactcaagg agcagaacaa cctgcttcag   27900
ccgggtgaag aactcacgcc tcagcgtcag atgcttatta atgccgaagc cagcttactg   27960
gaagcggtca agcgtaagtc cgctgaacag gcgaaggaga cactaagtt aatccagacc   28020 cagaacaagc aactagtcat agaccaagtg tatcagcgac gtctggctgg ggacaacgtg   28080
tccaccaact atgaggacct tccggtctca gatgctacag gagagttcaa acgttcagac   28140
atgaacaact atgcgtctgc caagctacag cagattgacc agatggacat ccctgaggct   28200
gctaaggacg cccagaaggt ggcattgtta agggctgaca ctaacaacgg tccgttccgt   28260
aatgccttcc agacgcttac tcaggacgct gctggtgagt ggcaagctgc ggtcatccgt   28320
ggacagtacg acccagacaa gatgaaacgc ttcgagtctc ttcgtcgtgc ctacactcag   28380
gacccttcaa gtttcgctgc tctgtatcct gaccaagctc agttgttctc tacgttcgac   28440
cagatggaca gatgggtct ggaccctcag acgatgattg aagctgataa gcaagctgca   28500
agtcaaagcc gtgagatgcg catggagtca gacaaggcgt ggcaggagtt gaagaacgac   28560
tctcggaata aggaccttc gcgtcttcct acgtctctgg acgcaagtgc tcgtaaggtc   28620
tgggactcat ggtactatcg tacaggtaac gctgacgctg caactcagca gactcaacgc   28680
tggctgaatg agaacaccgt aacgttccag tctgatggtt ctgatggtaa gtccatcggc   28740
atggtgtcca agcaccagct tatggtcggg gataacccag agtcgtggca ggtgggtcga   28800
gacattatcg acaccgctcg taagcagctc attaaggaca acccttgggt agtgaactct   28860
cagttgtccg ttgttgaaca gaacggctct atcttcctcc aagacgctac ggggactatt   28920
cgtattcgat acgataaaga acttgtaggt aaactctacc gcgaacaaca gcagaaggta   28980
caagatgccg catatgctca ggcagaacgt gacgctaaca agcgagcgcg tatcgtcggg   29040
actaaagctg ctggtgacaa acgtcgagct gaccgagagg ccaacatcga gaagagcggt   29100
gggatgtaca atgacgtctc actggagggt atcgcaaacg tactaattgg taaggagtaa   29160
cataatggcg actcgtggta ttcgcaataa caatccgggt aacatccggg taagtaagga   29220
ccaatgggaa gggatgactg gagatgatgg cgcattcgtc accttcgata gtccagagtc   29280
tggcgtccga gctttaggta aaaacctgct gtcctacggt cgccaaggtt atgactccat   29340
cgagaagatt atcaaccgat gggcacctcc taacgagaac gacactaagg cttatattga   29400
ctcagtggtg gctgcaactg gtattccagc tacccagagt ctagacctat ctgaccctga   29460
caccctgtct tctctggcac aagctatcag cttccatgag acaggatcac ggtacgaccc   29520
tgaagtctat cagaagggag tcgcacgggc actcaatggc attagcccaa agactccacc   29580
agtaagcgct aacgtatttg acgcactcac ggaaggactc aaggctaaac ctaaagtaga   29640
tctgggcgag aaccttccga ccgctgctgg tctaaacatt gagggtcaag cacctgaagc   29700
tcccaacgaa tcgttcggtg agatgttcta taagtctact ggcgagacca tgcaggaacg   29760
agaggatcgc tctacgtggt tcggtttcgg ctcggctaca gaagctgaag tgaagaactc   29820
tatggtcggc gtggctatcc gcgctggtca gaccgaggac tcacttgatg tcattggcga   29880
```

```
tgtgtttaac ccgacccgct ggaacaacca taagtggtct cgtgaggagc tggaccagat    29940
tcgtaacgct ggagttcttc ctcagtatta cggggtcatt actggtggct cccctcagaa    30000
cctgaccgag cttattaact tggcgcttga gaatcagaag ttggaccaag agaaggccaa    30060
ggctgggatt ggtgctcagt tagctgctgg tgtgattggg gctggcgtgg accctctgac    30120
ctacgttcct attgctgggc aggtaggcaa aggtgggaag ctagtcaaca agatgttcac    30180
tgtggcagct cagtctggtg ctctggctgg tgtgtctgag atggcccgta cctcagtggc    30240
tggtggtgat gctcatgtgg ctgaagctat ccttggcggt gctctcttcg gtggtggcat    30300
gactgctatc gctgatgggt taggcagagc cttaggccgc aacactaatg agtttgctgg    30360
cccagctaca cgtctggaag ctcgtgagac cgctcgtaac gttgatggtc aggacctgtc    30420
tcgtcttcct attcaggaag gtgagcagac ctttagtcat caaggtgtta agttcgcaga    30480
cgttccgaac gagccgggta gtgtacgact ggaagatggt tcaatcctga ttggtgagaa    30540
tcctctgaac cctcagacac gtaaagtctt tgacgaagtg attgagcctg aacgtgccgc    30600
tgctggtgtg aaccttggtg ggctgactga gattggcctg aagctgcttc ggtccgaaa    30660 ccctgagatt cgtggagtag ctgctgactt agtacgttca ccgactggta tgcagtctgg    30720
ggcctcaggt aaaataggga caactgcgtc agacgtattc gagagacttc gtgctgtgga    30780
ccatcggttc tacaatgaca tcgacgatgc ggttactgag gcactaaagg acccgtactt    30840
ccagacagca ttctggcgag actctggcgc attccgtcaa gacatctatc agcgcgtgtc    30900
tatggctatc gaagatggta gcggaaacct gaaggctgaa ttgactccgg gagaactgaa    30960
agtctatgac ctgctgaaga accagtttga cgccaagcgt gagatgatgg agaaccccgc    31020
tatgtttggt cgcccagacg ctcagtctat cttttccgggt agccgcttca agggaacata    31080
cgtcccgcat gtgtatagca accagatgaa ggagctgtac atcaaggagc ttgggagtcc    31140
agaggcacta caggaggcca tcaagaagtc atggttgacc agctatgcgt ctcgacctga    31200
agtcaagaaa cgtgtggacg aggcactctt agaggctgac cctacgttga ctccagaagg    31260
acttgcggct gcggtcgata agtacgccaa cgataaggct tatggtatct ctcacaccga    31320
gcagttcgag cgttcatccg taatggaaga gaacatcaat ggtctggtgg gtctggagaa    31380
caacagcttc cttgaggctc gtaacctgtt cgatagcgat atgtcaatcg tcctacctaa    31440
cggtcagacc ttcagtgtca acaacctgcg tgagtgggac atggacaaga ttgtcccggc    31500
ctacaaccgt cgagttaatg gcgatattgc tatcatggct ggtacaggca agaccacgaa    31560
ggacatgaag gacttggttg agaccctgat gaacaaggct ggggatgacg gtaagttgaa    31620
aggtgaagta tctaccttac gtgacacttt gaagattcta actggtcgtg ctcgacgtga    31680
tggtgctgat gatgcggcct tcgctaccgt gatgcgcaca atgacagacc tatcgttctt    31740
cgctaagaat gcctacatgg gtgttcagaa cttaacggag attggtggta tgctggctcg    31800
tggtaacgtt cgtgcaatgc ttcatggagt cccaatttc cgtgacctag ccttccgtaa    31860
caagaaggtt ggggcctcag agattaagga cctgcacaat gttatcttcg gtaaggaact    31920
ggatgactca atccgtccgt ctaaacagga tgtcattgac cgtctgcgat cttacagtga    31980
cctcggtcgt ggtacagcta cagctctggg gactgccaag tattacactg gcgaacttgc    32040
agtacgctct ccgttcacta aagtcctcaa cggtacgacc aactacctgt tagatgctgg    32100
acgtcagggc ttcctgtctg acatcgtgga gcatagcctg actggtagta agcgtaagtt    32160
cgatgaccgc tggctgaaga ccgctggtat ctctgacgag cagtggaagg gcattaagtc    32220
cctaatccgt gagtcagtga ctcgtggtcc agacgggaag tacaccatca aggataagaa    32280
```

```
ggcgttcagt caggacccaa gggctatgga cctctggcgt atgggtgaca ccatcgctga    32340
cgagacgtta ctccggcctc ataagctgtc aaacatggac gccaaggctt atggtcctct    32400
cgctaagact gtccttcagt ttaagaactt cgtcatcaag tctatcaatg ggagaaccat    32460
gcgaaccttc tataacgcca cgaagaacaa cagagcgatt gacgctgcac tgtcgaccgt    32520
gatgtctatg ggtctggctg gtatctacta catggctcag gcgcatgtca aggcttatgc    32580
tatgcaggat ggtcgagacc gtgactacct taagcaagct ctggacccaa cgatgattgg    32640
ctatgcggcc ctgtcccgta gttcacatct tggtggccca cttggggtag ctaacattct    32700
gggtggaatc gctgggtatg aggacactaa gatgctccgc tcgtcaatcc ttccgcgctc    32760
acctaccgag aagacggaga agccaatcgc ctttggtgct gcttccagtg gtccggtaat    32820
gaatgtggtc ggcaacttcc ttgagcaggt cccggctttc ggctatgctg ctaacgttgg    32880
tgctacggct tacaacttgg cgggatacct caaggctgat acccgtgtca acgagcgaga    32940
ctacatgacc gggatgtata acacgttccg tgaacttgta ccgaatgacc cgattaccca    33000
gaagttgctg cttggaacgt tgaggagca gggcatccac atcaaggact aaactatcac    33060
tataggaaac tggaggcgct accataggtc tccgtttaaa tcacaaagga gcataatgt    33120 ccacgattac acaattccct tcaggaaaca ctcagtacag gatagagttc gactacctag    33180
ccagaacgtt tgttgttgtt acgctggtga atagctctaa ccctacccctg aaccgtgtac    33240 tggaagttgg tcgagattac cgattcctta atccaacgat gattgagatg ttggctgacc    33300
aatcaggttt cgacatcgtt cgtattcacc gtcagactgg aactgactta gtggtagact    33360
tcaggaatgg ctcagtgttg acagctagtg acctgaccaa ttcagagctt caggctatcc    33420
atattgcaga agaaggtcga gaccaaacgg ttgacttagc gaaggaatat gccgatgctg    33480
ctggtagctc tgctggcaac gctaaggata gcgaggacga atcacgccga atcgctgcga    33540
gtatcaaggc agctggtaaa attggctata ttacccgtcg ctccttcgag aaaggcttca    33600
acgttacaac atggaacgag gtcctgctat gggaagagga tggtgattat taccgctggg    33660
atggtacgct tccaaagaac gttcccgctg gttcaactcc tgaatcatct ggtggtattg    33720
ggctgagtgc gtgggttagt gttggtgatg cgtcacttag agcaaacctg gctgatagtg    33780
atggcgctaa atacataggc agtggagaaa ggacattact tgagcacaac aatgatgttt    33840
tgcactcaaa agactttcca acactgcagg cagctataga tgcatctttg caaaaaaatg    33900
atctactggt gtctcctggc aattatactg aaaaagttac tattggaaac gcgcagttaa    33960
aaggtgttgg cggggccacg gtactaaaaa ctccggcaga cttttacaaac actgttcagg    34020 ttaatttagc tacacctcat tggcaattcc gccatagtgg tggttttgct atagatggtt    34080
ccgggacaac cggggccgta ggtattagtt ttgacccgtc agaccaatat tccgacgtc    34140 ataattttag tgatgtatac atccacaaca tcaacaaggc cattcagaag ccttccggga    34200
acatcggcaa tacttggaga aatattggga tatctacgtg tgattggggg tattacgcga    34260
ttagtggctc agagatgcat tgcggggccg ataccctcta caatatccac ttcgatggca    34320
tctccaccta tgcagtctat ctagacggca ctgtcgataa tggcgggggg ggcgcatggt    34380
ggcttaaaga ctccattatt gaggcttccg gaggtggcgg gatatactta aaaagtaaat    34440
cgggcgactg tcctacatct ccatgcgggg tatccaatat atggatggaa gcgatcgcaa    34500
catcaccggc tgttcaggta gacggcgtgg cgcaaaaacc gcgagttctc aagttggtag    34560
acacagcgat attctttgct gagtattctt atctcaacaa catcgagcta tccaactcca    34620
```

```
acttagtaac ttatggttgc cgttttgaca acgctgatgg caatcaggat attgtcgtgg   34680
atgcacaaag taccattgta gcccatgacg tgtatttaaa cggcagttct ggaaaggacg   34740
ttattgtgga gtccgtagca tcgcaatctg caacgatagc tgccacaaac ttatctctga   34800
ggggcaactt aacaagaggg agagtattta atacgccgac agggaataaa ttaatggcta   34860
tcacatttga ctcaggtagc cataattttt ctggcagcgg caccgttaac ggttcgactg   34920
tatctgacgg acttcacgcc gctacatgta ccgaattttc attccccgga gccggtttat   34980
atgaaatggt agcgacaaga acaaccatta catccggtag atggtacgtg tggggagtta   35040
actcacgcct acaatctggc tcggcggata ttagtataac gtcaggtatt accatgggta   35100
gtgtttacac aaagccgggg gagtggatta gcactttcgg tgtaggaaag gcatctacca   35160
ctggcactgt agcgctatac gtttccacag gaggaggttc gggagctacg gtcagattca   35220
gtgacttttt catcgctgag tttacgacgc aagctcaggc tttagctttc gccaattcaa   35280
ggatgtcgtt atcataaaaa caacctcagc cgaatcgggt tatttatcat cagaacggta   35340
ttgaatcatc gaaggttgtg gaggtagagg ctaactacac gttgaccaac gtatgataac   35400
aactttgggt cacggacgac ccgctttaaa ctggaggttt tatgattgag ttagacttca   35460
agaatgaggt cctcaaagcc tcgcctatcg tcgggaccgc tgcggctgat ggtgccagtc   35520
ggttcttctt tgggctaacg ctcaacgaat ggttctacgt cgctgctatc gcgtacaccg   35580
tggtgcagat tggcgtccta atttacaaga cgattaagag cggaggtaag acatgacgca   35640
gatggactta gagaagttcc tgttaatgct ggacacagaa cgtgctagac taatgctgca   35700
agacctgcgg gatgacacta agcgttcacc tcagctctac aacgccattg agaaactgct   35760
tgctcgacac aactttgtgt taagcaaggt gtctgtggac gagaagacgc tggcggatat   35820
ggaggccttg aacgaagagt acgataaggt gctttcagct actgaggata atgacaccgg   35880
gtatggtgtt caataagtgt tagactcaag gtcatcgtca ggtggccttt atggttaaca   35940
ctgactagtg gaggcgactc tacgttaaat ctgataaacc gggagggcaa ctatgctcga   36000 attttaaag agagcggctc cgtggttact tgcagcagtg atgtttgctg gtggctacca   36060
caccgctaac aataagtggg aggctaaggt caatgcagaa tacacctcga atcttaaggc   36120
atcggaagat acaaggcttg ctgtccaagc tgaagtcaac aaagtgtcca acggtttca   36180 ggacgaaatg tcctcgctgg aaggcagcac tgataggatt attgctgacc ttcagtctga   36240
caataagcgg ttgcgcatcc gagtcaaacc aacgagtgga accacgcaaa gtgacggtcg   36300
atgcttcatt gatggttacg ccgaacttga cgaacgagat gctaaacgtc ttatcgccat   36360
cggagtgaaa ggagacaagt ggattaaggc ccttcaagac actgtgagag ccttacagca   36420
agagaaggag gtgacgcatt gagtaaagac ttagtggcgc gtcaggcgct aatgactgca   36480
cgtatgaagt cagacttcgt gttcttcctg ttcgtcctgt ggaaagctct gtcgctccca   36540
gtcccgactc gctgtcagat tgacatggcg aagaaactat cggctgggga caacaggcgc   36600
ttcatcctac aggcgttccg tggtataggg aagtccttca ttacgtgtgc cttcgttgtc   36660
tggaagctat ggaacaaccc agacttgaag ttcatgattg tgtcggcctc aaaggagcga   36720
gccgatgcta actccatctt catcaagcga atcatcgacc tcatgcctca gcttcaggaa   36780
ctcaaaccta agcagggaca gcgagatgcg gttattagct tcgacgtggg acctgccaag   36840
ccagaccact caccttcggt taagtccgtt ggtatcactg gtcagttgac tggtagtcgt   36900
gctgacatcc tgattgccga tgacgtggag gttccgaaca actcagcgac tcaggctgca   36960
cgagaccgtc tatcagagct tgtgaaagag ttcgacgcta tcctgaagcc gggaggtacg   37020
```

```
atcatctatc tgggtactcc tcagaacgag atgaccctgt accgtgagct ggaaggtcgt    37080
gggtacacca ctactatctg gcccgctcgt tatccacgcg acaggaagga ctggcagtct    37140
tacggcgacc gtctggctcc tatgcttcag gaagagctgg aagaggaccc tgagtccttc    37200
tactggcgtc cgactgatga agtacgcttc gatgatacgg acctgaagga acgtgagctg    37260
tcctacggta aagctggctt cgctctacag ttcatgctta acccgaacct gagtgatgcc    37320
gagaagtacc ctcttaagct ccgtgacctt atcgtagccg acttggaccc agcgtccagc    37380
ccaatggtct accaatggtt gccgaaccct cagaacaagc gtgaggacgt tcctaacgtt    37440
ggactcatgg gtgactcgta ccacacgtat cagactgtag gttctgcctt cagctcatac    37500
acccagaaga ttctggtcat tgaccctagt ggtcgtggta aggatgaaac tggatatgcg    37560
gtactgtacc agctcaacgg ctacatcttc gctatggaag ttggtggcat gcgtggtggt    37620
tatgaagact ctacgctgga agccttggct aagattggtc gtaagtggag ggtcaacgaa    37680
tacgtcattg agggtaactt cggtgatggt atgtaccttg agttattcaa gcctgtagct    37740
gcccgtatcc atcctgctgc tgtaactgaa gtgaagagta agggtcagaa agaactccgc    37800
atctgtgacg ttctggagcc tatcatgggg tctcacagac ttatcgttaa cgctgccgct    37860
atcgtccaag actaccagtc agcctctgat aaggatggtg ttcgtaaccc tatctactct    37920
ctcttctacc agatgactcg tatctctcgt gaacgtggag cattggcaca tgatgaccga    37980
cttgatgcgc tggctatcgg tgtacagttc ttcgttgagt cgatggctaa ggatgccaac    38040
aaaggcgaac gtgaagtcac tgaggagtgg ctggaggaac agatgagaa cccacggaaa    38100 ggcttcgagt ccatccacac tgagttctgg gacaatgggg tccgggtaac tcacgatacg    38160
gacgacgagc ttggactagg gtcatacgtt acgttccact agctgaatga ataactatag    38220
gtgaaagctg cattaataag cagctagtaa cctatagtta ctaccagtct aacatactgt    38280
tttacaagga gtttggactt aactatcact atagggaaga cccccggtta cttatagtat    38340
tactatagtg aatatacata tgcagacttt atgcaagacc ttaggaggca gactccgagt    38400
tcttacctaa ggcttgcacc gatggaagga gggtgatatt aatcataatc cctccaatac    38460
agatagtcac cgaccataga tacaggaggt atgtagcata tggcaaagac caaagctgta    38520
cttaaagctc tggcgaccaa tcgagctaca tacaggtttc ttactgctgt tctacttgct    38580
gctggcgtta ctgctggaag tcagtgggtc gggtgggtcg agactctcgt atgttctctg    38640
gtctctcagt gtaattaacg caatcatgat aacaatcaac gaaaggaggt agggatggac    38700
gaggagtctt atgggtcgtt ctctgacgaa gattatcaga cggagtggga atacgcgcat    38760
tgaagaccta aggtcagttc atagctgacg ctactctact gaccttagct actgtagtca    38820
aggactttag gtaacacctt aagagaagct cacttagggt catcctactt attggtctat    38880
cctagtgtcg cctgacctac ggtccttgac ctacagtggc tgtggcctac agtagtgacg    38940
atgagttttg gacaaaaagt ttgagaccac atctcacac                           38979
```